United States Patent
Funk et al.

(10) Patent No.: US 12,303,178 B2
(45) Date of Patent: May 20, 2025

(54) SYSTEMS AND METHODS FOR DETERMINING THE CURE OF PMMA INTRAOPERATIVELY AFTER IMPLANTATION OF AN ORTHOPEDIC DEVICE

(71) Applicant: WAVETEST, LLC, Cincinnati, OH (US)

(72) Inventors: Daniel A. Funk, Cincinnati, OH (US); Quang-Viet Nguyen, Aldie, VA (US)

(73) Assignee: WAVETEST, LLC, Cincinnati, OH (US)

( * ) Notice: Subject to any disclaimer, the term of this patent is extended or adjusted under 35 U.S.C. 154(b) by 634 days.

(21) Appl. No.: 17/617,441

(22) PCT Filed: Mar. 11, 2021

(86) PCT No.: PCT/US2021/021941
§ 371 (c)(1),
(2) Date: Dec. 8, 2021

(87) PCT Pub. No.: WO2021/183782
PCT Pub. Date: Sep. 16, 2021

(65) Prior Publication Data
US 2022/0296289 A1  Sep. 22, 2022

Related U.S. Application Data

(60) Provisional application No. 63/111,318, filed on Nov. 9, 2020, provisional application No. 62/989,227, filed on Mar. 13, 2020.

(51) Int. Cl.
A61B 17/88 (2006.01)
A61B 17/00 (2006.01)
(Continued)

(52) U.S. Cl.
CPC ...... *A61B 17/8802* (2013.01); *A61B 17/1717* (2013.01); *A61B 17/72* (2013.01);
(Continued)

(58) Field of Classification Search
CPC . A61B 17/8802; A61B 17/1717; A61B 17/72; A61B 34/30; A61B 34/76;
(Continued)

(56) References Cited

U.S. PATENT DOCUMENTS

| 4,455,268 A | 6/1984 | Hinrichs et al. |
|---|---|---|
| 4,515,545 A | 5/1985 | Hinrichs et al. |

(Continued)

OTHER PUBLICATIONS

Lionetto et al., Monitoring the Cure State of Thermosetting Resins by Ultrasound, Materials (Basel), 2013, pp. 3783-3804, MDPI.
(Continued)

*Primary Examiner* — Jerrah Edwards
*Assistant Examiner* — Jose H. Trevino, III
(74) *Attorney, Agent, or Firm* — Hudak, Shunk & Farine Co. LPA

(57) ABSTRACT

The invention comprises a system for securing an implant to a bone comprising an implant which is affixed to the bone, a grout or bone cement comprising a composition that cures in an exothermic reaction and which is capable of securing the implant to the bone in a cured state, a device which provides access to the grout or bone cement in position on the bone and a tester which measures temperature over time to detect the exothermic reaction so as to determine when the composition reaches cure. The tester comprises a sensor joined to a circuit and to an indicator that emits a signal in response to a current emitted to the circuit by the sensor.

15 Claims, 23 Drawing Sheets

(51) Int. Cl.
- *A61B 17/17* (2006.01)
- *A61B 17/72* (2006.01)
- *A61B 34/00* (2016.01)
- *A61B 34/30* (2016.01)
- *A61L 24/04* (2006.01)
- *G01K 7/22* (2006.01)
- *G01N 25/20* (2006.01)

(52) U.S. Cl.
CPC .............. *A61B 34/30* (2016.02); *A61B 34/76* (2016.02); *A61L 24/046* (2013.01); *G01N 25/20* (2013.01); *A61B 2017/00084* (2013.01); *A61B 2017/00115* (2013.01); *A61B 2017/883* (2013.01); *G01K 7/22* (2013.01)

(58) Field of Classification Search
CPC ........... A61B 2017/00084; A61B 2017/00115; A61B 2017/883; A61B 17/1764; A61L 24/046; G01N 25/20; G01K 7/22
See application file for complete search history.

(56) References Cited

U.S. PATENT DOCUMENTS

| | | |
|---|---|---|
| 4,559,810 A | 12/1985 | Hinrichs et al. |
| 4,574,637 A | 3/1986 | Adler et al. |
| 4,590,803 A | 5/1986 | Harrold |
| 4,758,803 A | 7/1988 | Thomas, III |
| 4,874,948 A | 10/1989 | Cielo et al. |
| 4,891,591 A | 1/1990 | Johnston et al. |
| 4,904,080 A | 2/1990 | Afromowitz |
| 5,009,104 A | 4/1991 | Johnson |
| 5,145,250 A | 9/1992 | Planck et al. |
| 5,911,159 A | 6/1999 | Choo et al. |
| 6,644,122 B2 | 11/2003 | Borowczak et al. |
| 6,675,112 B1 | 1/2004 | Chadwick |
| 7,245,371 B2 | 7/2007 | Wang et al. |
| 8,419,640 B1 | 4/2013 | Saha |
| 9,297,789 B2 | 3/2016 | Djordjevic et al. |
| 2006/0123914 A1 | 6/2006 | Pena et al. |
| 2007/0154874 A1 | 7/2007 | Sherman et al. |
| 2007/0270786 A1 | 11/2007 | Higham et al. |
| 2009/0084978 A1 | 4/2009 | Chandler et al. |
| 2009/0112365 A1 | 4/2009 | Orr et al. |
| 2010/0087827 A1 | 4/2010 | Baroud |
| 2010/0110436 A1* | 5/2010 | Chandler ........... A61B 17/8802 702/176 |
| 2013/0035561 A1* | 2/2013 | Sharkey .................. A61F 2/389 600/561 |
| 2021/0302374 A1 | 9/2021 | Jack |

OTHER PUBLICATIONS

Yao et al., Power ultrasound and its applications: A state-of-the art review, Ultrasonics—Sonochemistry, 2020, pp. 1-20, Elsevier B.V.

Price et al., Polymerization of Methyl Methacrylate Initiated by Ultrasound, Macromolecules, 1992, pp. 6447-6454, vol. 25, American Chemical Society.

Arenas-Arrocena et al., New Trades for the Processing of Poly(Methyl Methacrylate) Biomaterial for Dental Prosthodontics, 2017, pp. 43-74, Chapter 3, Intech.

Dunne et al., Ultrasonic characterization of the mechanical properties and polymerization reaction of acrylic-based bone cements, Journal of Engineering in Medicine, 2007, pp. 251-261, vol. 221.

Mchugh, Ultrasound Technique for the Dynamic Mechanical Analysis (DMA) of Polymers, BAM-Dissertationsreline-Band31, 2008, pp. 1-146, Berlin.

* cited by examiner

| Temp | Cool | Hot | Cool |
|---|---|---|---|
| | V1>V2 | V2>V1 | V2>V1(LATCH+) |
| CMP1 | Off | On | Off |
| LATCH | Off | On | On |
| CMP2 | On | Off | On |
| AND1 | Off | Off | On |

FIGURE 3

First Derivative of Dental Cement Cure between In Vivo and In Vitro

|  | Run 1 | Run 2 | Run 3 | Run 4 | Run 5 | Run 6 | Mean | STD |
|---|---|---|---|---|---|---|---|---|
| In Vitro | 16:03 | 16:12 | 15:42 | 16:31 | 16:05 | 17:24 | | |
| In Vivo | 12:19 | 10:49 | 12:12 | 09:31 | 10:36 | 11:55 | | |
| Difference | 03:44 | 05:23 | 03:30 | 07:00 | 05:29 | 05:29 | 05:06 | 01:11 |

FIGURE 22

SYSTEMS AND METHODS FOR DETERMINING THE CURE OF PMMA INTRAOPERATIVELY AFTER IMPLANTATION OF AN ORTHOPEDIC DEVICE

FIELD OF THE INVENTION

The field of this invention is in the area of medical devices, and in particular, medical device systems relating to assurance as to the cure of bone cement during surgery, as well as to methods of use of the devices, including surgical methods using the system.

BACKGROUND OF THE INVENTION

The present invention addresses issues relating to a method for the determination of the state of cure of bone cement or grout used in present surgical procedures. The state of the art for determining full curing of the PMMA intraoperatively is problematic, as the state of cure is determined either by direct palpation of the PMMA edge or by allowing extra PMMA not used in the surgical implantation to harden.

Acrylic bone cement has been used in orthopedic surgery for over fifty years and is the standard of care for fixation of total joint arthroplasty. After mixing the liquid monomer with the powdered polymer, the cement converts from liquid to solid by an exothermic reaction. The duration of full polymerization is variable and depends on multiple factors, including temperature and humidity. The ASTM Standard specification for full cement curing in a testing environment is based on the temperature of the cement (shown in FIG. 1). The cure temperature ($T_{cure}$, i.e., the temperature where the cement is considered fully cured) is approximately halfway between the maximum temperature of the cement during curing ($T_{max}$) and the ambient beginning temperature of the cement ($T_{ambient}$).

it is desirable to be able to provide an improved in-vivo method to determine the full PMMA cure and to document that hardening of the PMMA has been achieved during surgery. More accurate determination would provide for decreased surgical time and better protection from PMMA implant bond breakage. No device or system is known which presently provides this assurance.

Presently, cement curing during implant surgery is determined either by palpating the cement edge or by allowing the remainder cement to harden in vitro. Both methods are imprecise and unscientific. Intraoperative observation by surgeons has noted that in vivo cement appears to cure faster than the remaining excess cement in vitro. This is likely because the in vivo cement is in a warmer and more humid environment.

The significance of cement curing time in vivo has become more important with recent investigations into the cause of aseptic loosening of a total knee tibial implant. It has been proposed that lipid infiltration between the tibial tray and the cement interface prevents the cement from interdigitating with the undersurface of the tibial tray, resulting in an area of de-bonded cement. Motion prior to full cure of the tibial tray cement can hydraulically wick lipids into the cement—tray interface. As a result, accurate determination of curing of the cement under the tibial tray before knee motion during total knee arthroplasty is important.

However, it is believed that the presumption that in vivo cement cures before in vitro cement has not been validated. Furthermore, the curing time of in vivo and in vitro cement has not been quantified. The present invention compares the cement curing time of a simulated in vivo tibial tray with that of an in vitro remainder cement using a novel means of temperature analysis.

Aseptic loosening of the tibial plateau base plate after total knee arthroplasty remains one of the primary reasons for revision surgery of total knee arthroplasty. There is evidence that breaking of the cement implant bond at the time of surgery is a contributor to the development of aseptic loosening. Movement of the knee prior to cement cure can be a cause of migration of lipids under the base plate and breaking of the cement implant bond. Recent focus has been on lipid infiltrating under the tibial tray. This infiltration prevents the cement from obtaining a secure mechanical bond on the tibial tray. New tibial implant designs have been developed to decrease the possibility of lipid infiltration. Motion of the knee prior to cement cure can increase the risk of lipid infiltration and subsequent debonding, even with the new tray designs, motion of the knee prior to cement cure remains a possible source of aseptic loosening. There is an ongoing debate whether certain implants are more susceptible to aseptic loosening or a two-batch technique with full cure of the tibial tray before proceeding with the remainder of the surgery should be the standard of care. The present technique to assess for cement cure in-vivo at the time of surgery is imprecise. The devices and methods described in this paper are unique and novel. When used in combination these methods and devices would help protect the knee from early motion until full cement cure.

Presently, determining the time of full cure of the cement intraoperatively is, at best, imprecise. The state of the art of using remainder in vitro cement to determine cure has changed little from the early days of arthroplasty. Waiting for the extra cement to cure is a time-honored artistic ritual for surgeons and staff.

The present invention confirms that the technique of using the external cement to determine curing of the in vivo cement is valid and that developing a method using temperature sensors to accurately determine tibial tray cement curing could safely shorten the operative time of total knee arthroplasty.

SUMMARY OF THE INVENTION

The present invention addresses issues relating to cure of bone cement or grout which is used in conjunction with present surgical procedures. In particular, in a first embodiment, the present invention provides a system having a jig which allows a user to access a substance in situ in a bone, and a sensor that allows the user to monitor a reaction of the substance and to receive an alert when a set condition has occurred.

In a more specific embodiment, the system of the present invention enables a surgeon to make an accurate and reproducible bead of cement which undergoes an exothermic reaction during cure. The system enables the user to place a temperature sensor in the cement in situ during major orthopedic surgery, such as, for example total knee replacement surgery. This system comprises a jig and sensor which is joined to an alarm to alert the user of the state of the cement.

A method of using the system is accomplished such as by the use of a jig and/or drill guide which is designed to work within an established work flow method, and by using a tester including a temperature sensor such as a thermistor, thermocouple, or other electronic device that converts a temperature into a signal that can be processed using either and analog or digital means. Typically, temperature changes are registered as voltage changes which can be analyzed using analog comparator circuits to provide outputs to a logic circuit operatively joined to an indicator, such as a display, light, alarm, haptic indicator or robotic surgical device. Alternatively, the temperature signals can be digitized using an analog to digital converter (ADC) and the digital representation of the temperature is analyzed to drive a logical indicator.

The concept of an in-situ temperature sensor that monitors the state of the chemical reaction progress for PMMA cement that has been applied between the medical device and the bone while in-vivo (i.e., within the patient anatomy, and preferably at or within the actual implant cement interface) is novel. The analysis of the temperature signal from the in-vivo measurement to determine unambiguously, the state of the cement cure point is also novel in that it uses a plurality of conditionals related to the cement temperature, but does not depend on the absolute temperature, which can vary greatly depending on the application and environment in which the cement is used.

BRIEF DESCRIPTION OF THE DRAWINGS

FIG. 3 is a logic table for the cement cure;

FIG. 22 is a chart showing the time differences from runs shown in FIG. 21; and

DETAILED DESCRIPTION OF THE INVENTION

The standard means for stabilizing orthopedic implants used in total joint arthroplasty is grouting with an acrylic (poly methyl methacrylate—PMMA) material. In use, the PMMA is supplied in two parts: a powder monomer and a liquid catalyst. These two components are mixed during surgery and proceed from a liquid to a solid at varying rates depending on multiple factors such as temperature and humidity. The PMMA in its compliable state is applied to the bone ends with the implant then being pushed onto the bone with the PMMA between the bone and implant. After hardening, the implant is considered fixed to the bone and motion is allowed. Motion prior to PMMA hardening can lead to lipid infiltration underneath the implant which breaks the bond between the PMMA and the implant leading to loosening and possible need for revision surgery. The present state of the art for determining full curing of the PMMA intraoperatively is crude. This is ascertained either by direct palpation of the PMMA edge or by allowing the extra PMMA not used in implantation to harden. It is desirable to be able to provide a better means to determine the full cure and to document that hardening of the PMMA has been achieved during surgery. More accurate determination would provide for decreased surgical time and better protection from PMMA implant bond breakage.

Figure 1:
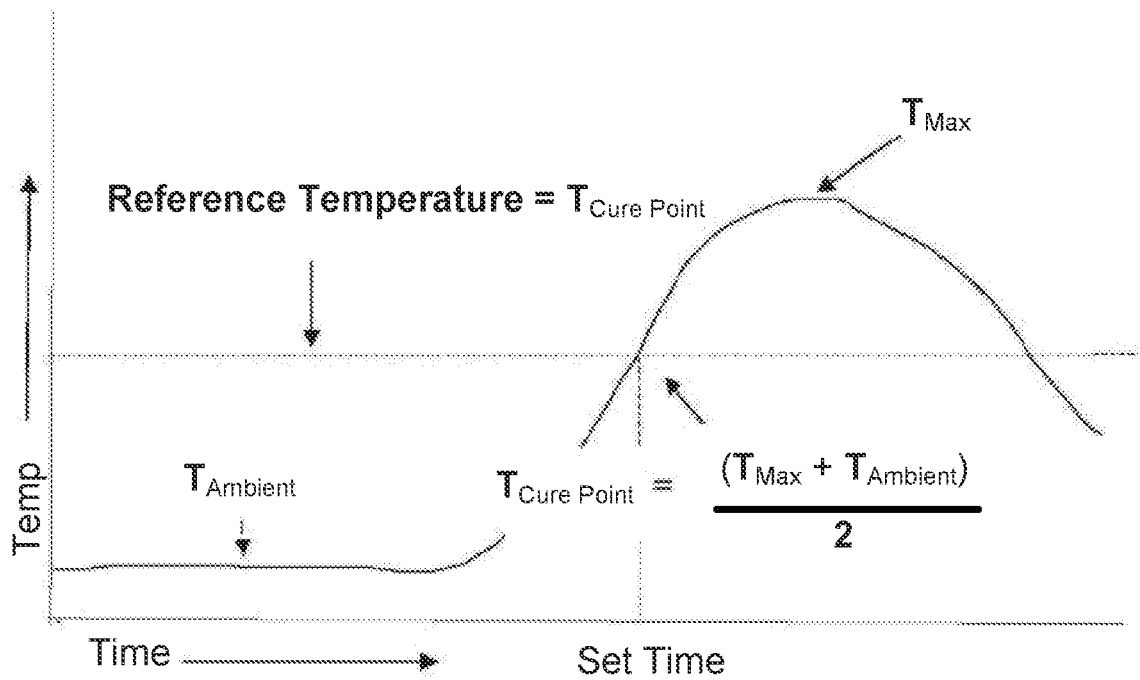
FIG. 1 is a plot of time vs temperature for the cure of PMMA after mixing.

PMMA undergoes an exothermic reaction during cure. During the phase transition of PMMA from liquid to solid (curing) the exothermic reaction has a thermal curve shown in FIG. 1.

PMMA cure temperature is represented by Reference Temperature ($T_{Cure\ Point}$) which is determined in a calculation between the maximum temperature and the ambient temperature. This cure point has been standardized for Orthopedic PMMA as referenced in the ASTM Designation: F451-16, "Standard Specification for Acrylic Bone Cement of the Joint in Preparation of Finishing the Surgery."

The present invention uses a tester to monitor the temperature of the PMMA after placement of the orthopedic implant onto the bone. This is accomplished by insertion of a temperature variable resistance device having a sensor, such as a thermistor which is a component of the probe into the PMMA in situ. The system of the present invention also includes a guide to provide access to the cement actually used to stabilize the bone construct (i.e., "in situ"). The current flow changes are registered in the thermistor with the temperature of the PMMA and can be calibrated to specific parameters.

Figure 2:
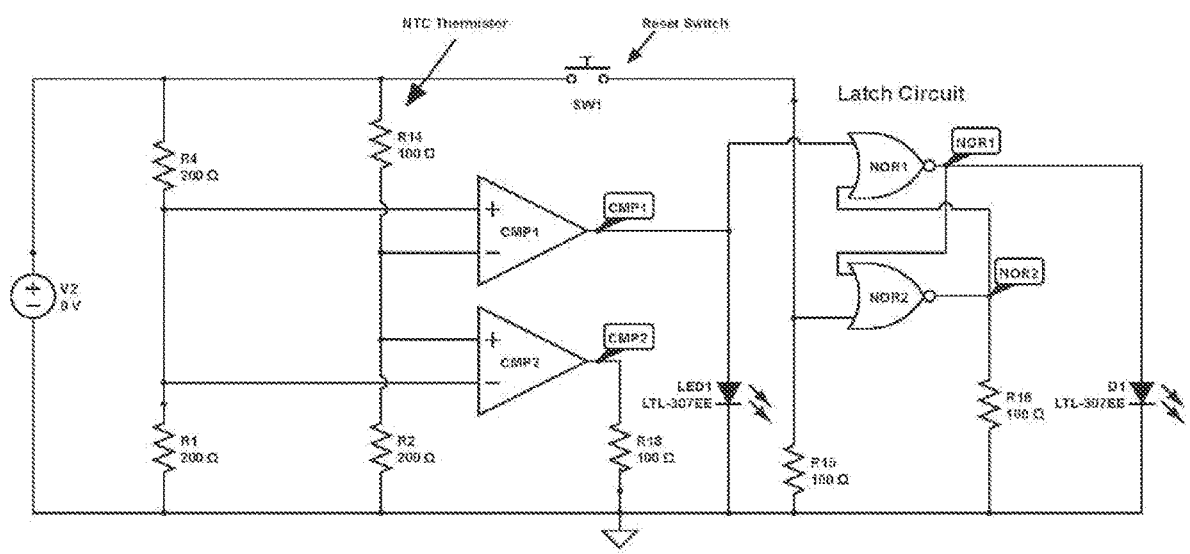
FIG. 2 is a diagram showing a circuit for a cement cure sensor in accordance with the invention.

A preferable temperature sensor for use in the present invention is a semiconductor-based negative temperature coefficient (NTC) thermistor. Positive temperature coefficient (PTC) sensors can also be used along with metal thermocouples, or even P-N junction-based diodes. The NTC thermistor is convenient to use as it has been highly developed to provide a low-cost and accurate sensor (up to 0.02 degrees C. accuracy) in a compact package such as small bead buried inside a flat hermetically-sealed casing comprised of thin polyimide tape. FIG. 2 shows a schematic diagram describing a NTC variable resistor whose resistance decreases with increasing temperature. The resistor R1 provides the voltage of the reference temperature ($T_{Cure\ point}$). The voltage across R2 is variable in response to the resistance thermistor in series. As the thermistor is heated, the current will increase and the voltage reading for R2 will increase. Using solid state comparators CMP1, the two voltages are compared. A lower V1 to V2 ratio indicates that the PMMA temperature is below the Reference Temperature ($T_{Cure\ Point}$) and a higher V1 to V2 ratio indicates PMMA temperature above the Reference Temperature ($T_{Cure\ Point}$). FIG. 2 illustrates a circuit for the sensor of the present invention. Note that the temperature signal processing described above can also be implemented using digital means as described in the sections below.

When the PMMA temperature is low, CMP1 will be on and CMP2 will be off, whereas when the PMMA temperature is high CMP1 will be on and CMP2 will be off.

The output of the comparators is then analyzed through a logic circuit. CMP1 is attached to the set lead of a digital latch. When the Set is initiated by a positive (on) signal, the latch is initiated, and the output of the latch remains positive (on) until the reset is initiated. As a result, once the reference temperature ($T_{Cure\ Point}$) is reached, the output of CMP1 turns positive (on) and remains positive(on) even when the temperature is below Reference Temperature ($T_{Cure\ Point}$) during cooling. The output of the LATCH and CMP2 are then analyzed through an AND Logic Gate. The output of an AND Gate is negative (off) until both leads are on. The final logic output follows the logic of FIG. 3.

Following the PMMA temperature cure curve, as the PMMA progresses past the $T_{Cure\ Point}$ LED1 is turned on which indicates that the PMMA has cured the joint can be safely moved. Continuing with the temperature curve the thermal response will cool since the reaction is complete. The circuit has primed the Latch Circuit after the first pass through of the $T_{Cure\ Point}$. When the PMMA temperature passes through the $T_{cure\ point}$ a second time as the PMMA cools LED2 is turned. This indicates that the PMMA reaction has stopped and cement is fully hardened.

In order to properly place the sensor in the cement in place on the bone, the system of the invention may further comprise a jig 10 that is used during the preparation for implantation stage of the surgery. Ideally, as shown in FIGS. 4-10, the jig 10 has a bottom stage 12 which consists of an inner drill guide 14 and an anterior guide hole 16. There are bone fixation pins 18 on the inferior surface 22 for fixation on the cut bone surface. There is also a posterior shelf 24 for assistance in fixation of the pins 18 into the tibia. An anterior stage 26 overhangs the tibia.

Figure 6:
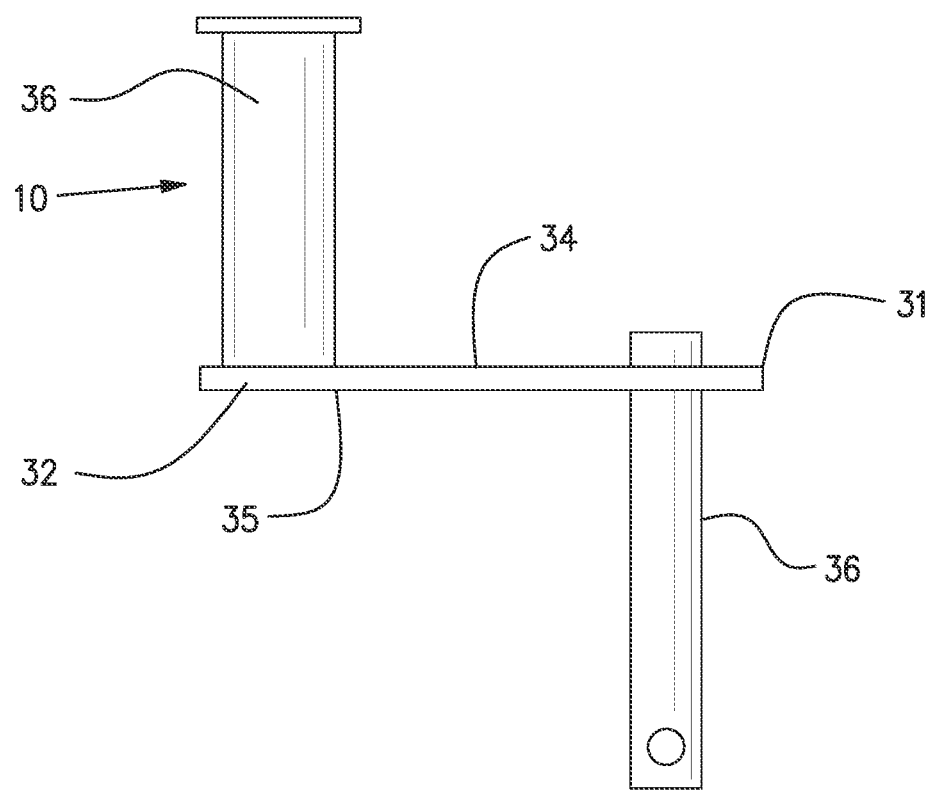
FIG. 6 shows a top view of a top stage of a jig in accordance with the invention.
Figure 7:
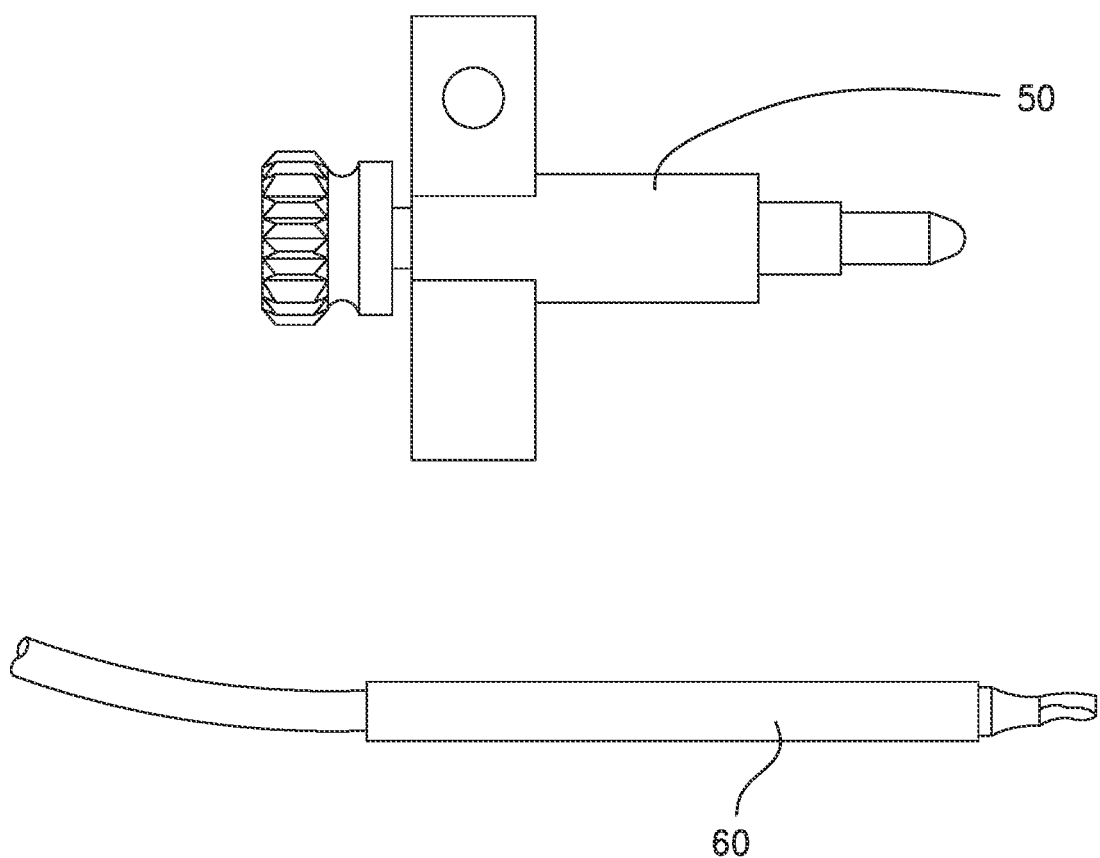
FIG. 7 shows; a side view of a probe and temperature sensor in accordance with the invention.
Figure 8:
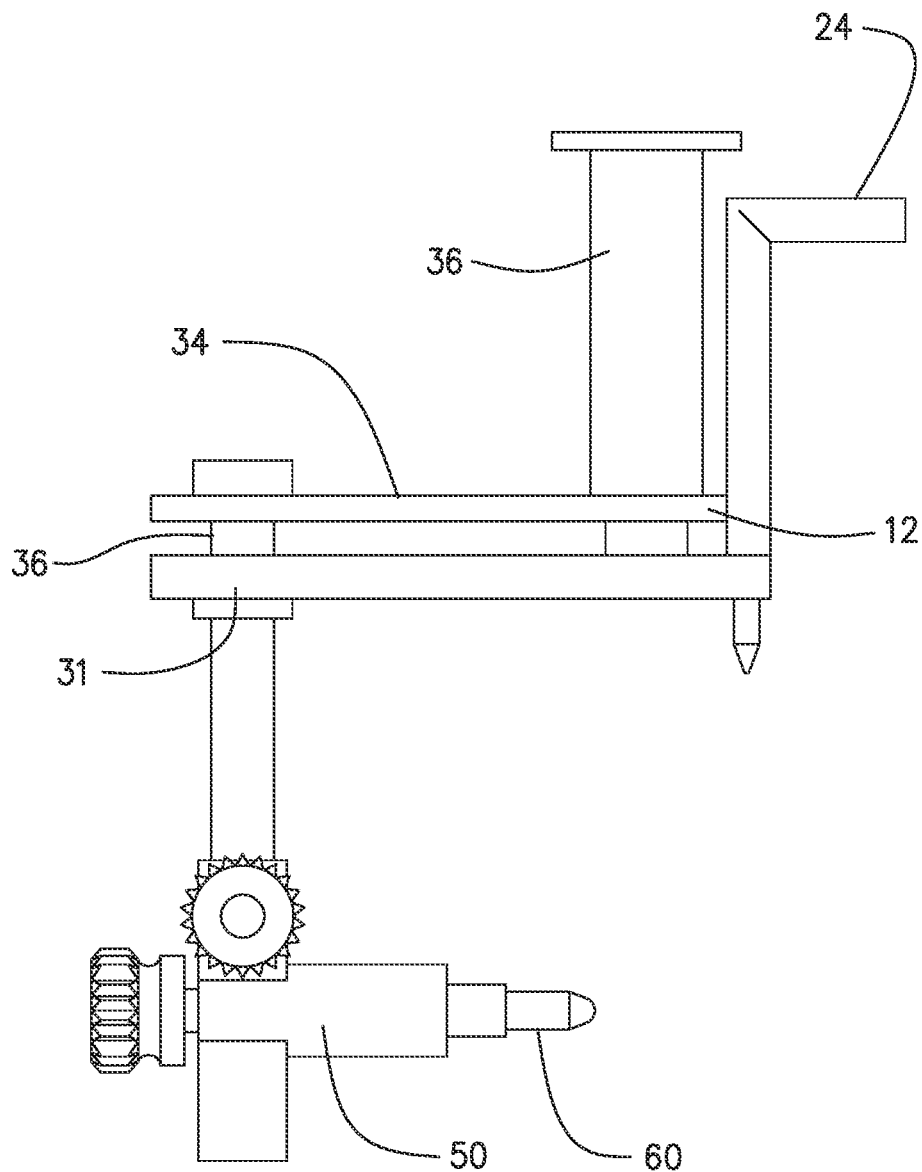
FIG. 8 shows a side view of the jig assembly of the present invention.
Figure 9:
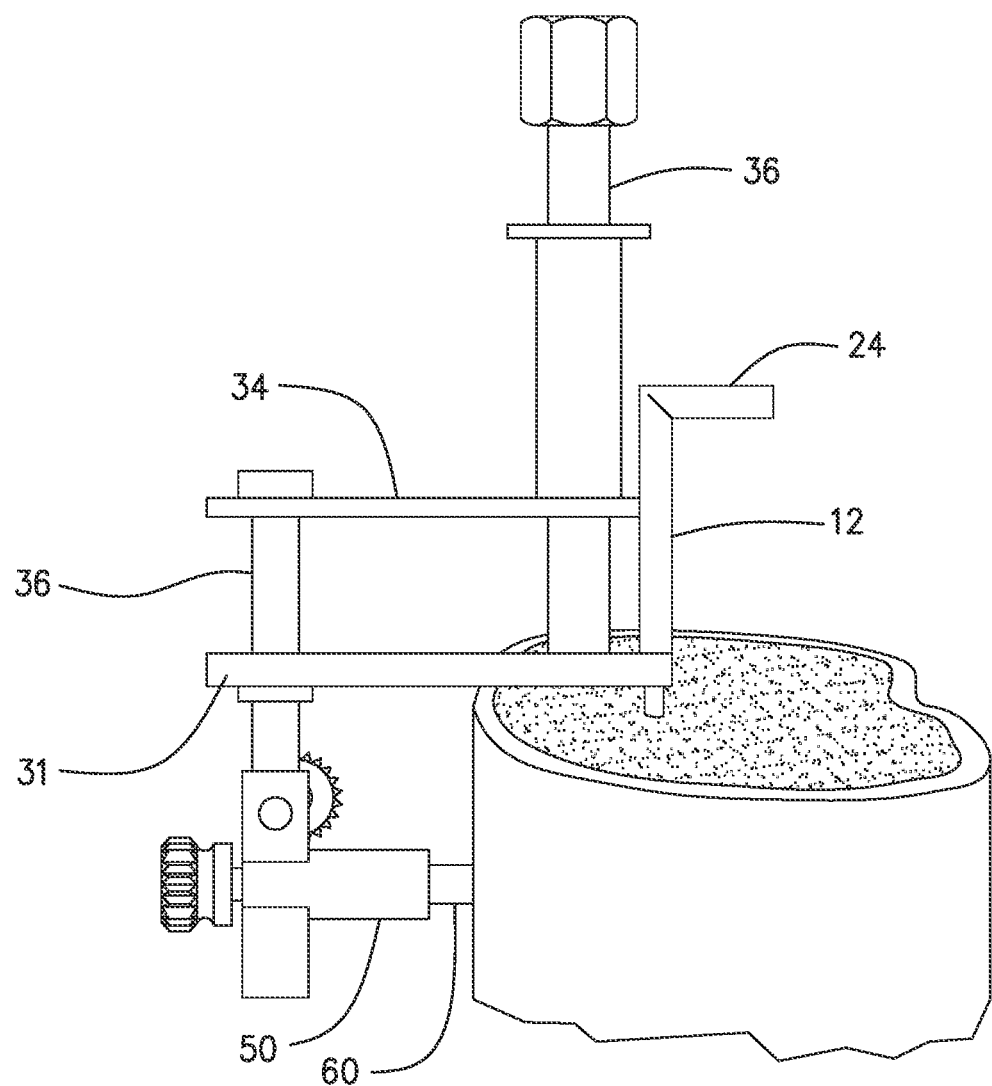
FIG. 9 shows a side view of the jig assembly of FIG. 8 in position on a bone.
Figure 10:
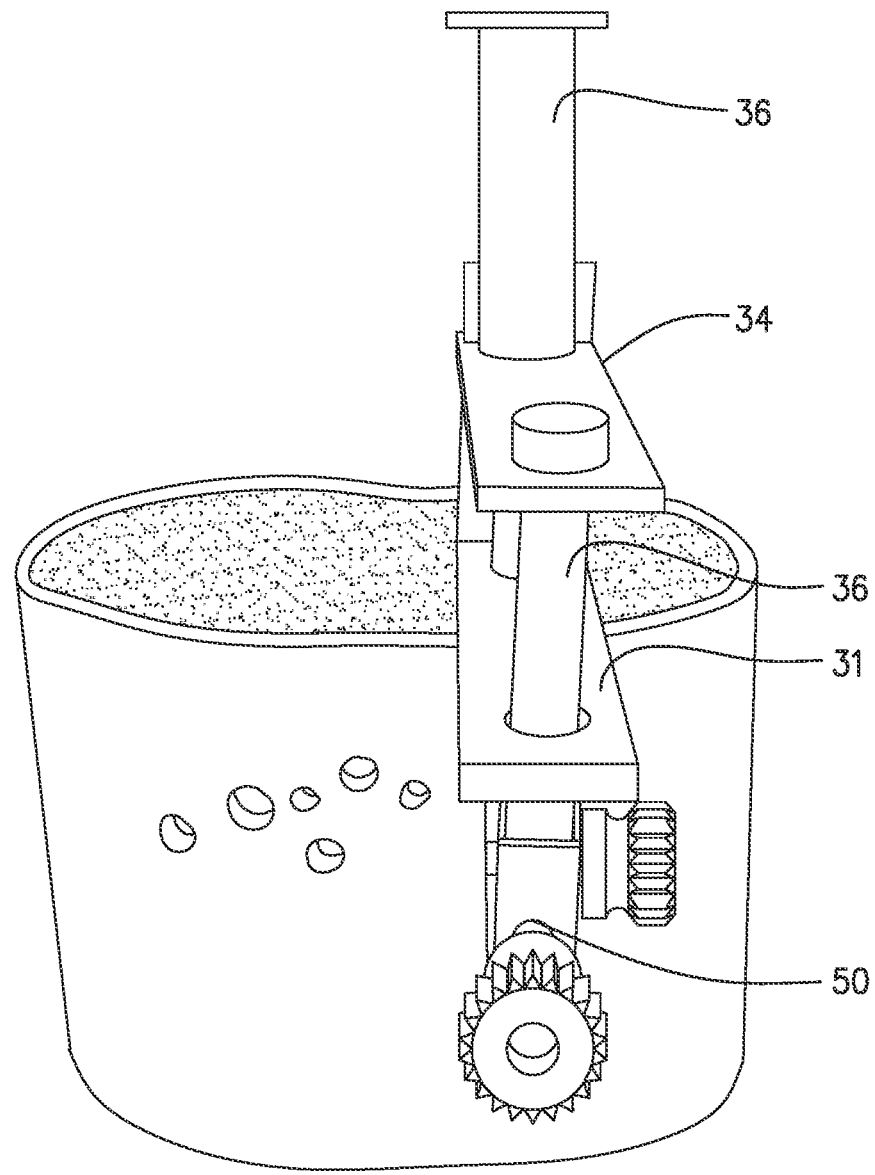
FIG. 10 shows a front view of the jig assembly and bone of FIG. 9.

FIG. 6 illustrates a top stage 32 which consists of a flat plate 34 which is the preferably the same dimension as the bottom stage 12. On the posterior aspect of the top stage 32 is a top stage drill guide 36 which fits over the drill guide 14 of the bottom stage 12. This has a surface to be used for a drill top on its superior aspect. The anterior portion 31 of the top stage 32 has a guide rod 36 which can slide in the anterior guide hole 16 of the bottom stage 12.

FIG. 3 illustrates an insertion probe 50 and a temperature sensor 60. The temperature sensor can be separate from, and integrated into, the insertion probe which serves to check the opening made in the bone and as well as to carry the temperature sensor. The insertion probe 50 can be connected and disconnected to the inferior aspect 35 of the guide rod 36. The insertion probe 50 faces the anterior tibia and is sized to enter the guide pin hole 16. The temperature sensor 60 can be inserted into the guide pin hole 16 either through the insertion probe 50, such as through a cannulation, or after removal of the insertion probe 50.

Method of Use

Figure 4:
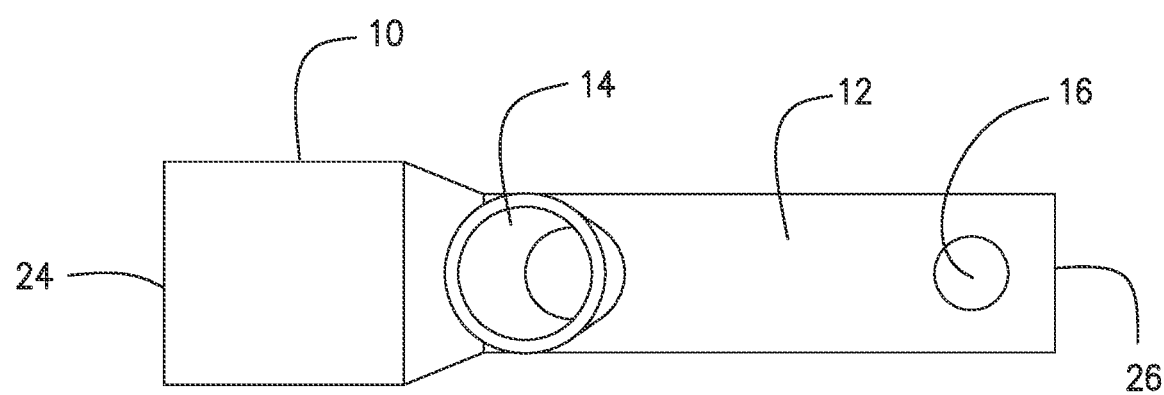
FIG. 4 shows a top view of a bottom stage of a jig in accordance with the invention.
Figure 5:
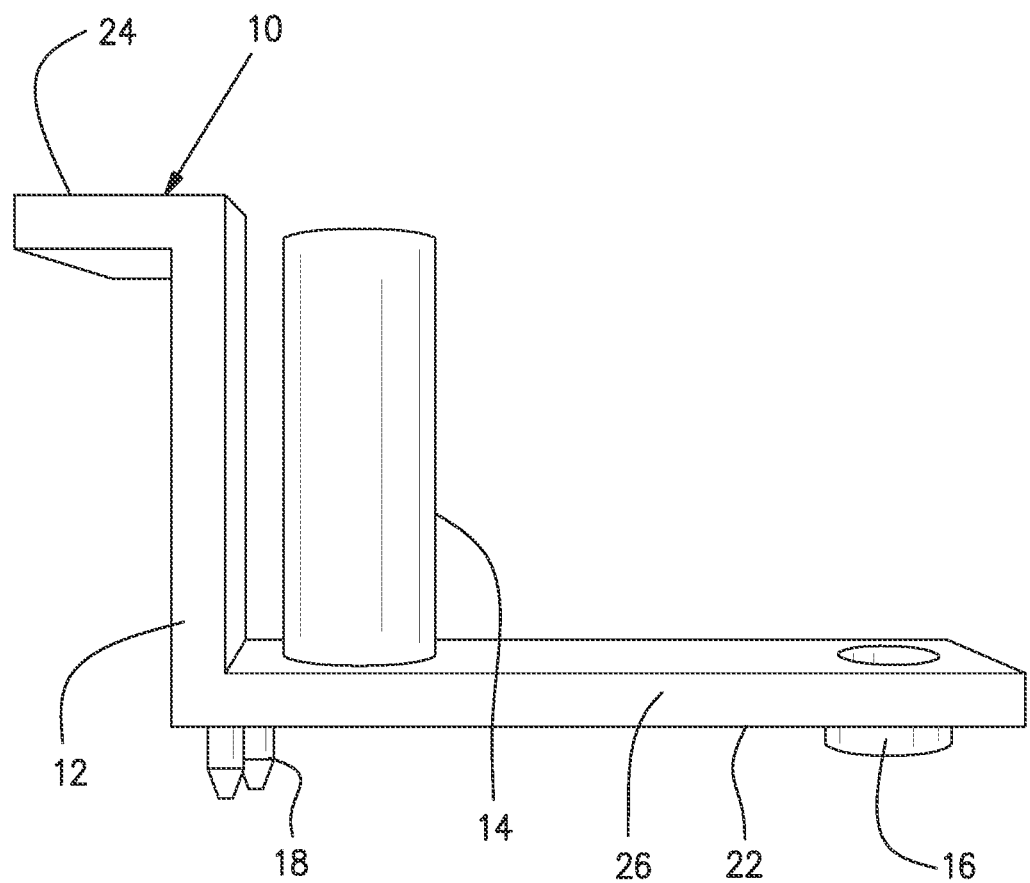
FIG. 5 shows a side view of the jig bottom stage of FIG. 4.

The surgical technique using the device jig will now be detailed. The surgical procedure is initiated and steps prior to use of the jig of the present invention are unchanged from the prior art surgical technique. It is anticipated that the present jig will be utilized after final trialing of the implant and just before cement application. At this point in the surgery, the fixation pins for the tibial cutting guide have been removed leaving the holes open. As is illustrated in FIG. 4, the jig device of the invention is assembled by placing the top stage on the bottom stage, sliding the guide rod from the top stage through the guide hole on the anterior bottom stage and placing the larger drill guide of the top stage over the drill guide of the bottom stage. The guide pin probe is then attached to the inferior aspect of the guide rod. At this point, the probe is inserted into the guide pin hole to confirm the hole and/or bone status. Then, the temperature sensor can be used, either separately or as a component of the insertion probe. To measure bone cement cure, the temperature sensor should be contained within the cement in an accurate and reproducible manner. There is no known existing device intended to perform this function. The system of the present invention enables a surgeon to make an accurate and reproducible bead of cement in which to place a temperature sensor during total knee replacement.

The jigs of the present invention comprise a drill guide on the surface of the proximal tibia which allows a tunnel to be performed from the tibial cut surface distally. There is a concomitant anterior tibial drill guide such that a probe can be placed from anterior to posterior connecting with the tunnel drilled from superior to inferior. The confluence of the two tunnels forms a pocket into which a temperature sensor can be inserted. Once the temperature probe is confirmed to be in the pocket, the probe is secured in such a manner that it will not back out until it is actively withdrawn. The temperature probe is than connected to the temperature monitor device previously described. The device utilizes the drill holes which are performed to hold the tibial cutting jig in place during preparation of the knee for implantation of the total knee arthroplasty. This drill holes are typically 3 mm in diameter and run from the front surface of the tibia to the posterior aspect and run parallel to the tibial cut surface. The pin holes are variable in distance from the top of the cut tibia distally. The described device consists of two stages which are placed on the top surface of the tibia with an adjustable arm anterior to the tibia. The two stages comprise of a bottom stage which is designed to lay flat on the cut tibial surface a top stage which can be guided onto the bottom stage.

After assembly of the device the guide rod is extended to its full length and the insertion probe guided into the fixation pin hole. The bottom stage is then lowered on to the cut surface and bone fixation pins pressed into the bone surface. The length of the total combined top and bottom drill guide is the length of the distance from the bone surface to the level of the insertion guide. A dowel or drill with collet is then placed through the drill guide to perform a hole from superior to inferior which intersects at the tip of the guide probe.

Figure 11:
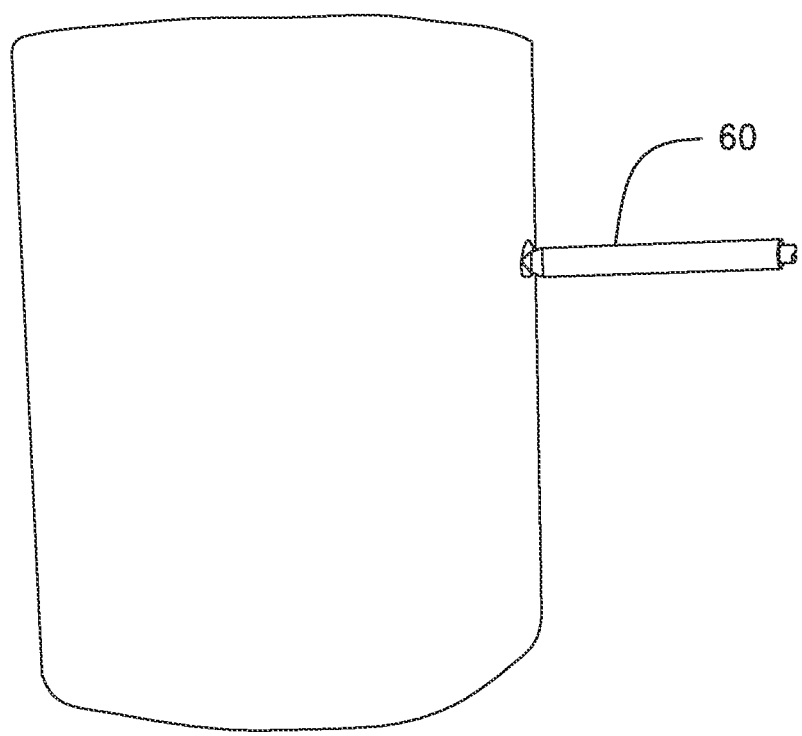
FIG. 11 shows a side view of the bone following removal of the jig with a temperature sensor in position.
Figure 12:
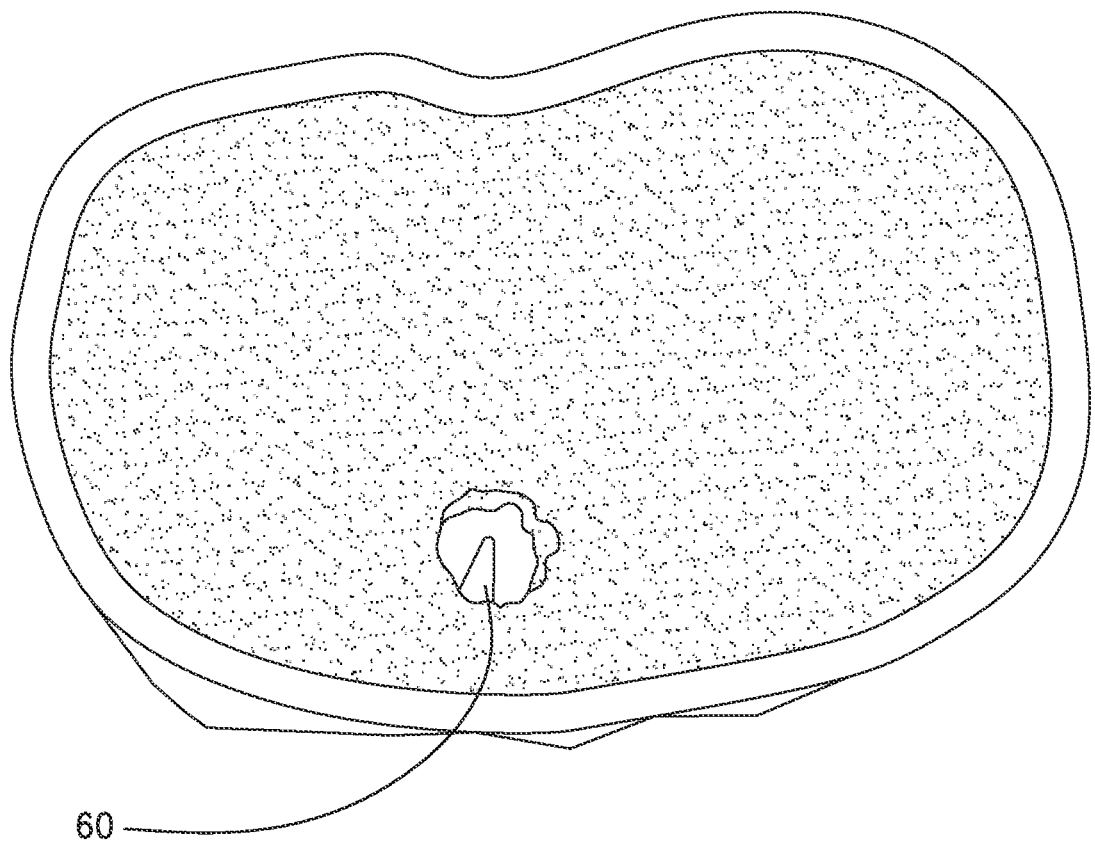
FIG. 12 shows a front view of the bone and temperature sensor of FIG. 11.

The bottom stage has a tubular drill guide perpendicular to the tibial surface on its posterior aspect. The anterior portion of the stage overhangs the anterior tibia and has a guide for use by the top stage. On the bone surface of the bottom stage are holding pins designed to provide fixation into the bony surface. There is a shelf to provide the user the ability to push the pins into the tibial cut bone posterior to the drill guide. At completion of the cement hole from superior to inferior, the temperature sensor is inserted through the pin fixation hole into the superior-inferior tunnel in the tibia which has been prepared by the jig. After confirmation of the correct placement of the temperature sensor the sensor is fixed in position by either mechanical means or use of a hydraulic balloon type catheter. (FIGS. 11 and 12)

The sensor is then attached to the previously described temperature sensing circuit. The surgeon then continues with the remainder of the cementing technique in a standard fashion ensuring that cement is placed into the cement hole. The implant is position and impacted and the temperature circuit monitored. After cure of the cement as documented by the temperature of the cement reaching the cure temperature, the sensor is removed from the patient. The remainder of the surgery is performed as per standard protocol. Postoperative care is dictated by surgeon orders.

Figure 13:
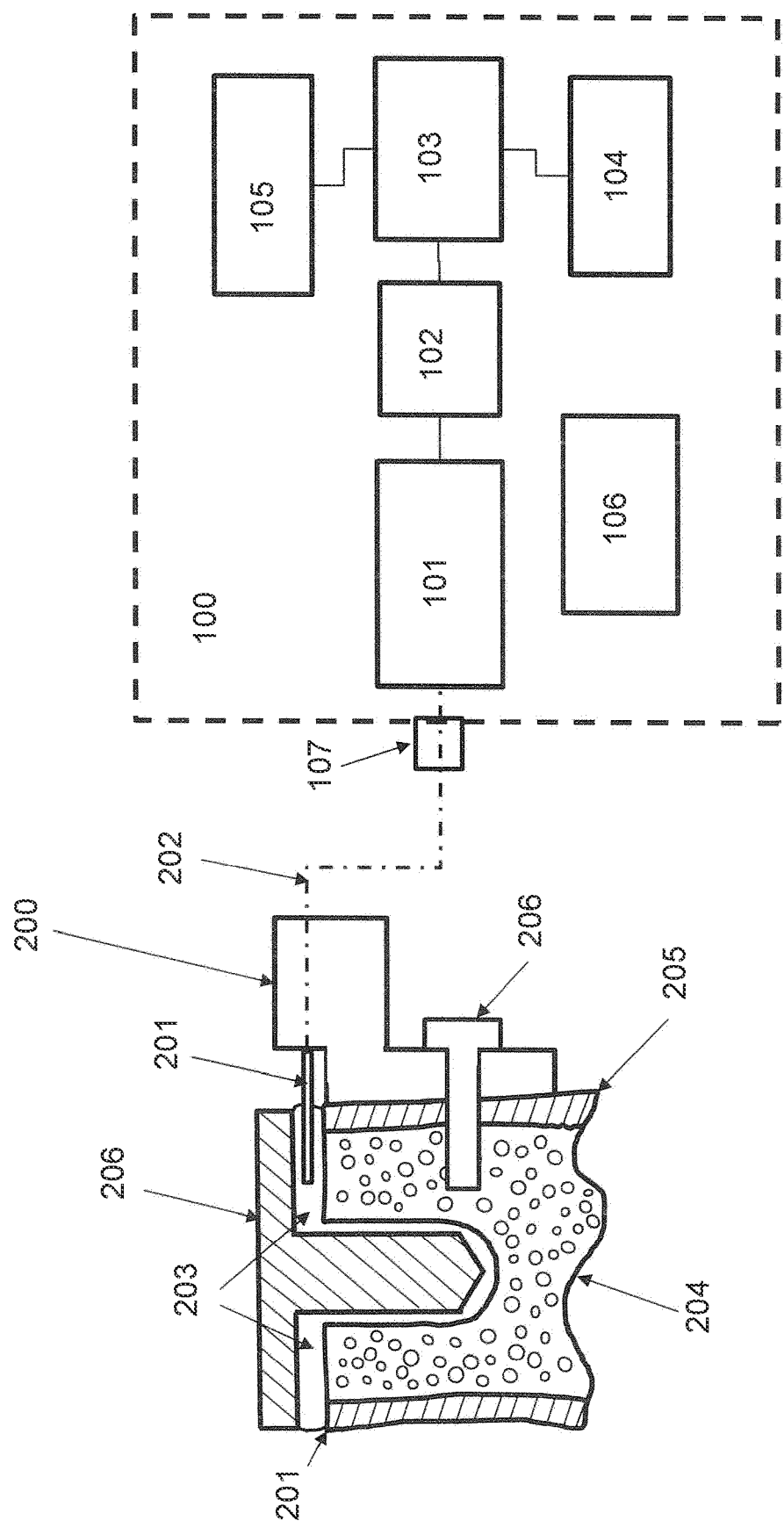
FIG. 13 shows a schematic diagram of an alternate embodiment of the present invention where the signal processing is performed using digital electronics effected using a microcontroller unit (MCU)

FIG. 13 shows a schematic diagram of an alternate embodiment of the present invention that utilizes a digitally based signal processor and display 100, comprising an NTC signal conditioner 101, which provides an analog signal to an analog to digital converter (ADC) 102, and a programmable micro-controller unit (MCU) or similar central processing unit (CPU), provides the means to determine if the cure point is reached via a series of IF statements. The MCU is connected to an external reset switch 104, and a set of light emitting diodes (LED) 105, used to indicate when the system is armed and ready, and also provides indication of when the cure point is reached. A battery 106 provides the electrical power for operation. The temperature sensor (typically, an NTC) 201, is fixed to the bone using a holder jig assembly 200, which provides a secure mount to attach the sensor 201 to the outer bone 205 and inner bone 204, such as by via temporary fixation screw(s), k-wires, or tacks 206. The sensor probe 201 is placed in the interior of the cement mantle 203, while the cement is still freshly applied and has not yet started giving off any heat due to the exothermic reaction. The cement mantle 203 attaches the metal implant (device) 206 to the tibial plateau 201 via grouting between the two hard surfaces. The temperature is sensed by the sensor probe 201, and the electrical signal is fed through a sensor cable 202 to the sensor signal processor and display 100, via means of a detachable sensor connector jack 107. The jack permits the sensor probe 201 and mounting jig 200 with cable 202 to be installed separately from the main sensor processor and display 100. Advantageously, the action of plugging in the sensor connector jack 107 into the sensor signal processor and display 100, turns on the electrical power to the processor and display, thus eliminating the need for a separate power on/off switch.

Figure 14:
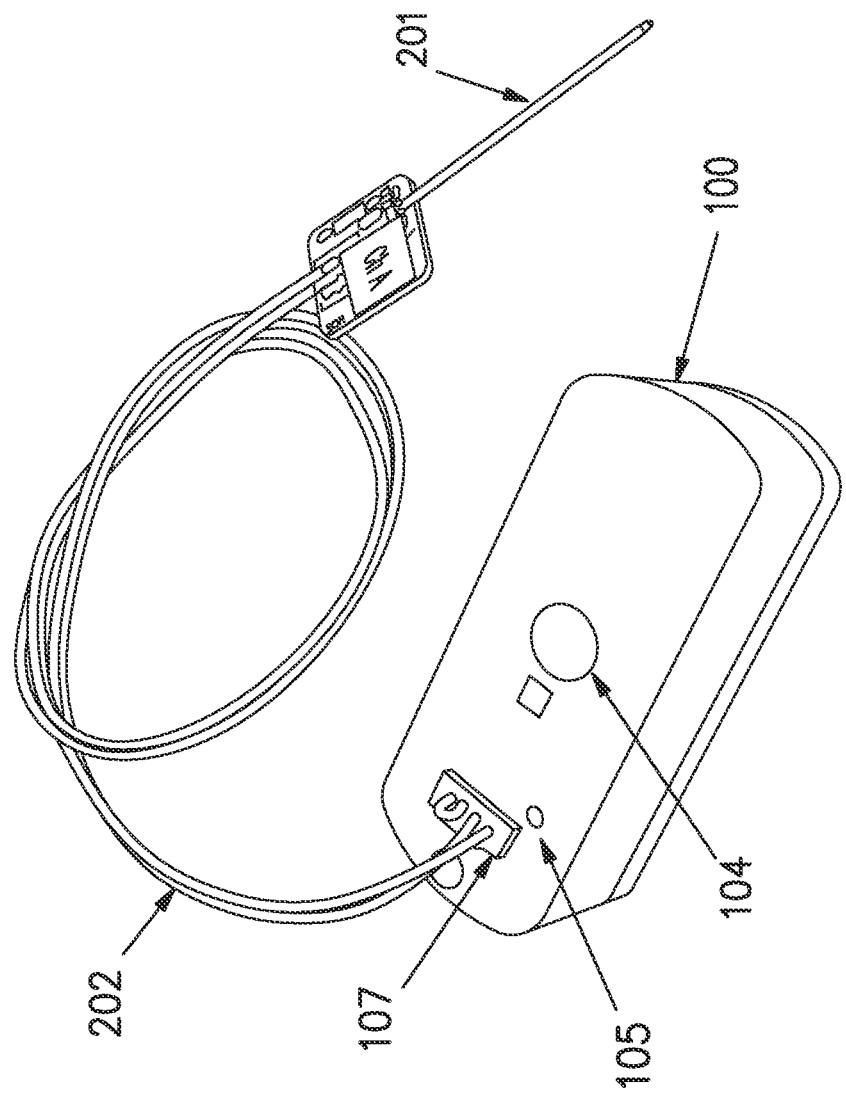
FIG. 14 is a photograph of a prototype MCU signal processor and attached sensor probe with cable.

FIG. 14 shows a photograph of a 3D printed prototype of the temperature sensor signal processor and display unit 100, showing the sensor probe 201, the cable 202, the connector jack 107, the reset switch 104, and the LED display lights 105 (one for 'ARMED' and one for 'CURED') to show the status of the device and the logical state of whether or not the cement has cured. For reference, the prototype is about 50 mm in length and 25 mm in height and is very compact and portable.

Figure 15:
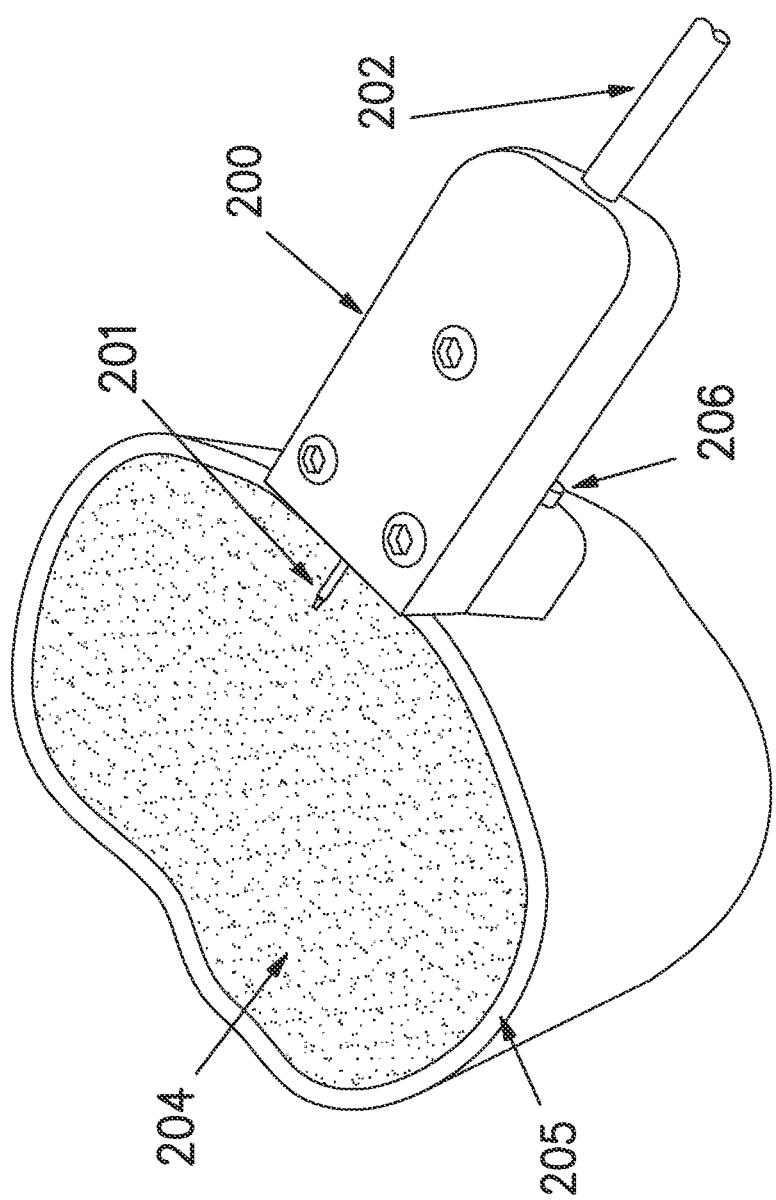
FIG. 15 is a photograph of a prototype sensor holder jig attached to a simulated bone representative of a tibial plateau.

FIG. 15 shows a photograph of a prototype 3D printed temperature sensor holder jig 200 with sensor probe 201, and sensor cable 202. The jig 200 is attached via temporary fixation screws 206 to a simulated tibial plateau comprising inner bone 204 and outer bone 205. The temperature sensor probe 201 is a thin (0.5 mm thick×2 mm wide) polyimide (Kapton) tape which encapsulates a small NTC thermistor and two electrically conductive flat metal wires. The extended length of the sensor probe 201 can be varied via use of different manufactured lengths of probe tips 201. In practice, the temperature holder jig 200, sensor probe 201, sensor cable 202, and fixations screws 206 could be packaged in a sterile single-use disposable package, or alternatively, some portion of the instrument or sensor system could be sterilized and re-used. The sensor probe tip 201 is thin and flat and is coated with a sterile surgical release agent, such as a lubricant (e.g., silicone grease), so that it can be extracted from the cured cement mantle easily by a simple pulling motion.

Figure 16:
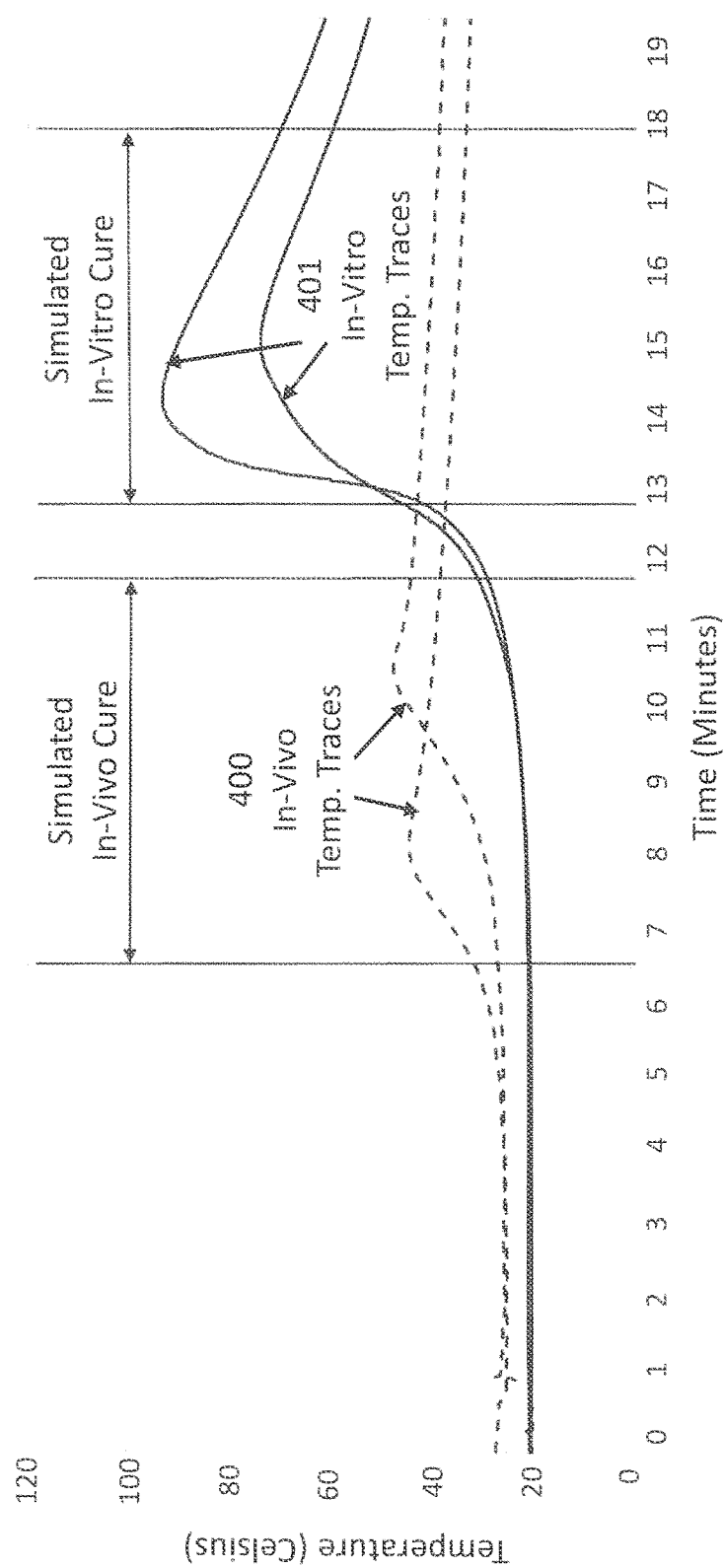
FIG. 16 shows measurements of the cement cure process in simulated bone in-vivo compared to in-vitro.
Figure 19:
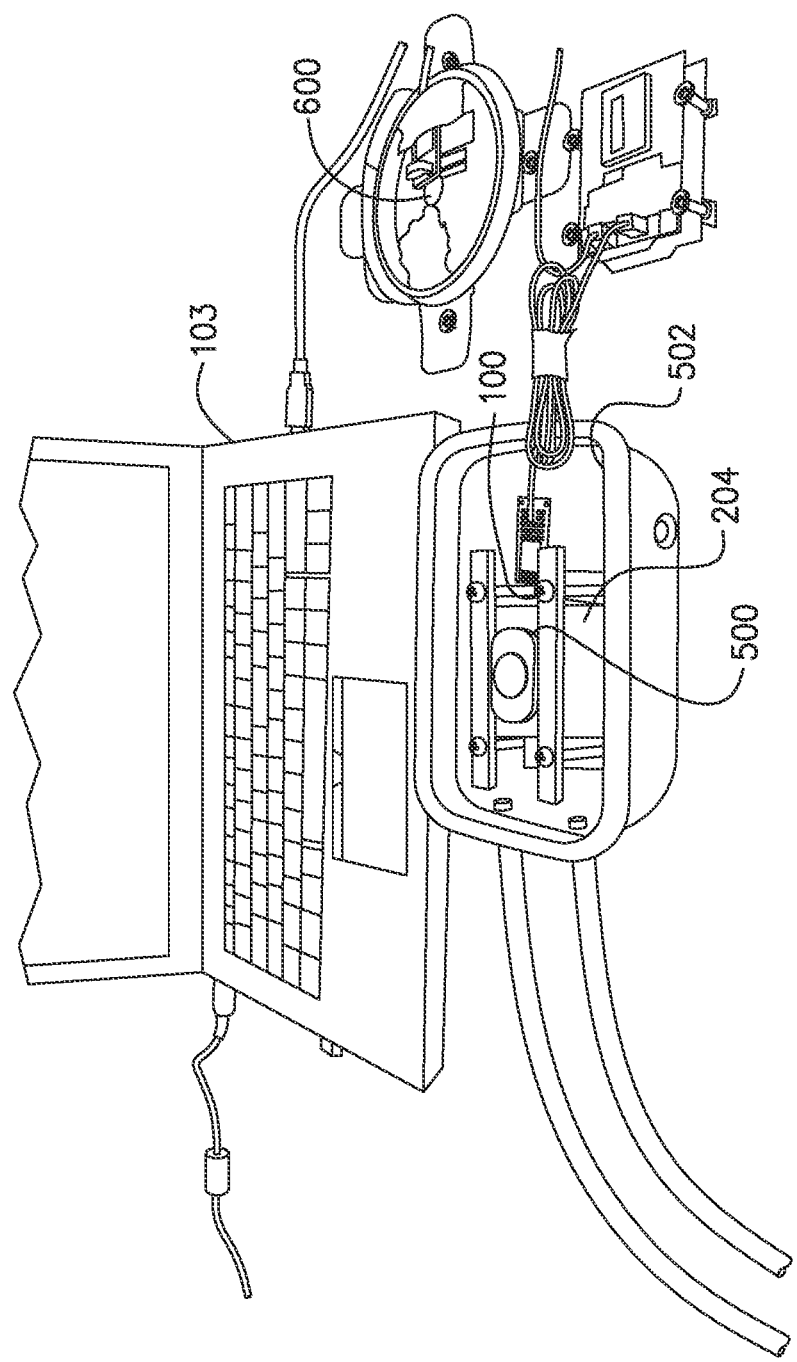
FIG. 19 is a photograph of a set-up for a simulation of the in vivo procedure in accordance with the present invention.
Figure 20:
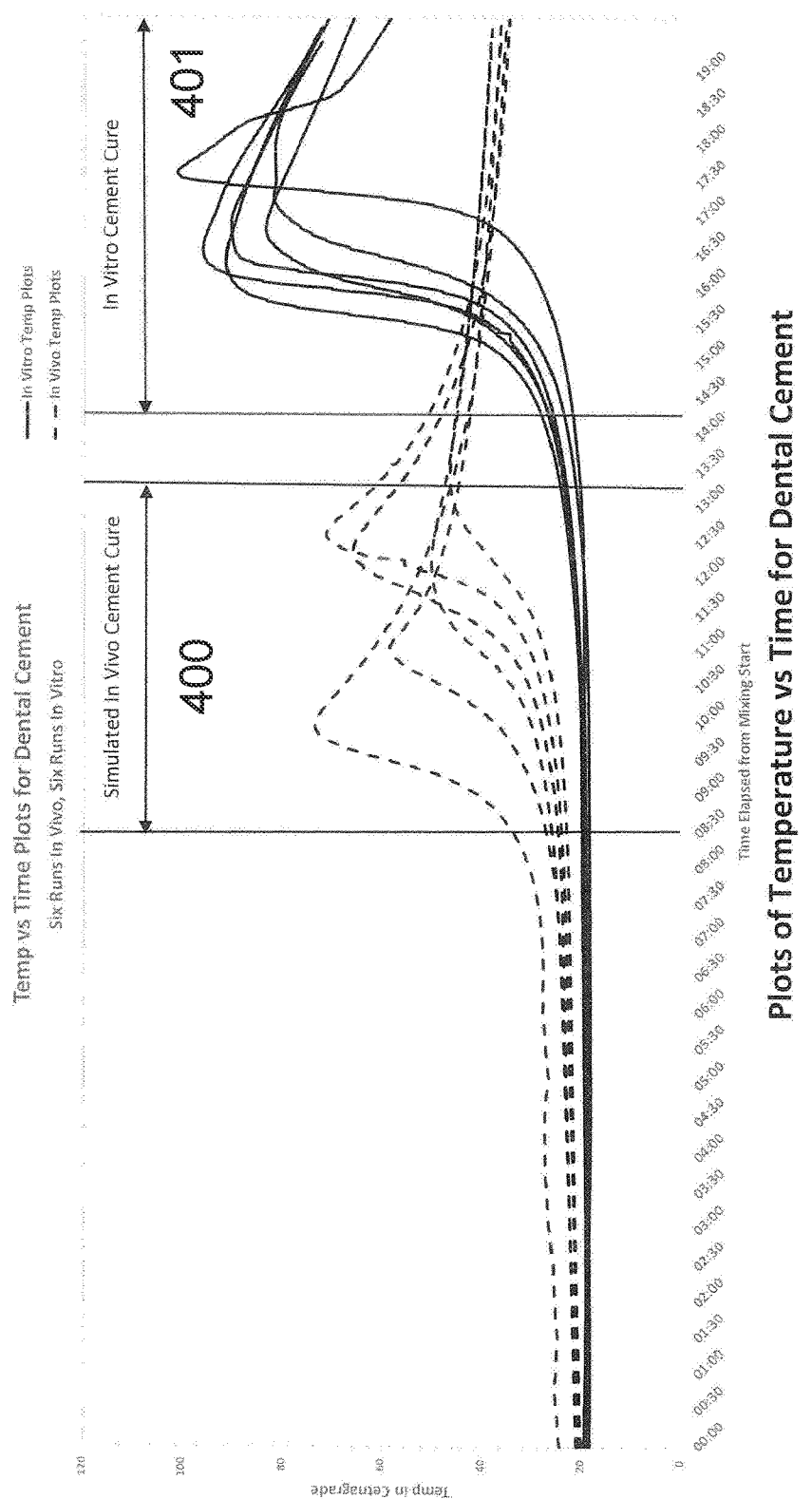
FIG. 20 shows measurements of the cement cure process using dental cement in in-vivo simulated bone.
Figure 21:
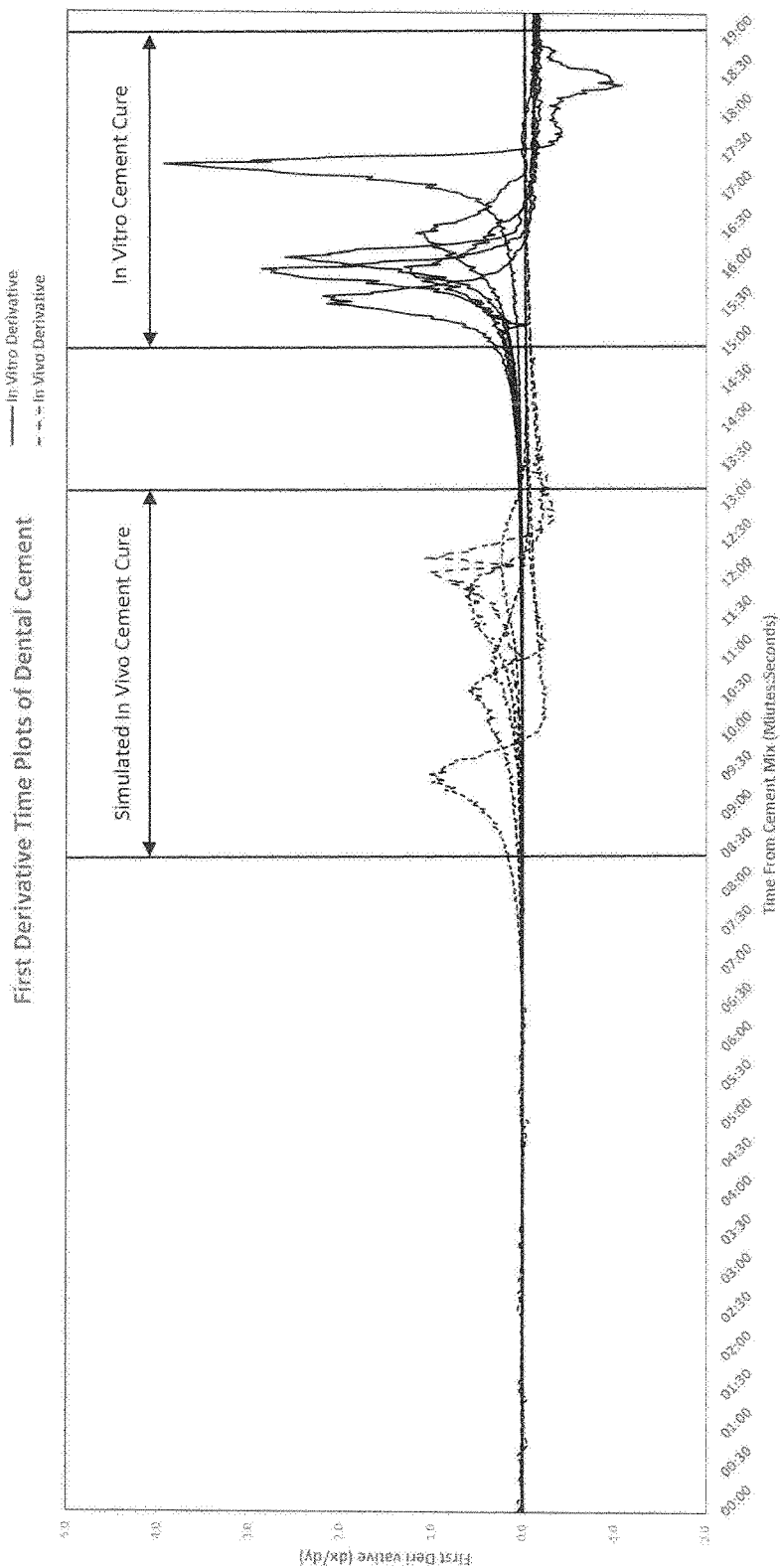
FIG. 21 is a plot of the first derivative for time vs temperature for in vivo and in vitro demonstrations of the invention.

FIG. 16 shows measured temperature data from a simulated bone and PMMA cement curing experiment wherein the temperature of the sensor probe is measured in-vivo 400 and in-vitro 401 for two runs at each condition. Similar data is shown in FIG. 20 for six experimental runs under simulated in vivo conditions using dental cement and bone cement respectively. The horizontal axis represents the elapsed time in minutes and the vertical axis represents the sensor temperature in degrees Celsius. The in-vitro traces 400 are measured in the cement mantle of a stainless-steel tray 500 and simulated bone in a water bath 502 held at a constant temperature of 32.2° C. The water bath level is held at depth of 25 mm below the surface of the simulated bone interface. FIG. 19 is a photograph of the experimental set-up used in the example described hereinafter. The in-vitro temperature traces 401 represent temperatures from a small 2 g globule sample of PMMA cement from the same mix as the in-vivo 400 traces except that it is external to the simulated bone. The temperatures are measured using the Steinhart-Hart equation using a known voltage (5.0 V) and known resistance (10 k ohm) in comparison with the NTC thermistor with a known Beta(28/85) constant of 3,435 K, recorded at 10-bit ADC resolution and a rate of once every 2 seconds. From inspection of the plots in FIG. 16, and the chart of FIG. 22, and according to the guidelines from ASTM standard F45-16, it is apparent that the in-vivo measurements reach their cure point approximately 4 to 6 minutes sooner than the in-vitro samples.

Figure 17:
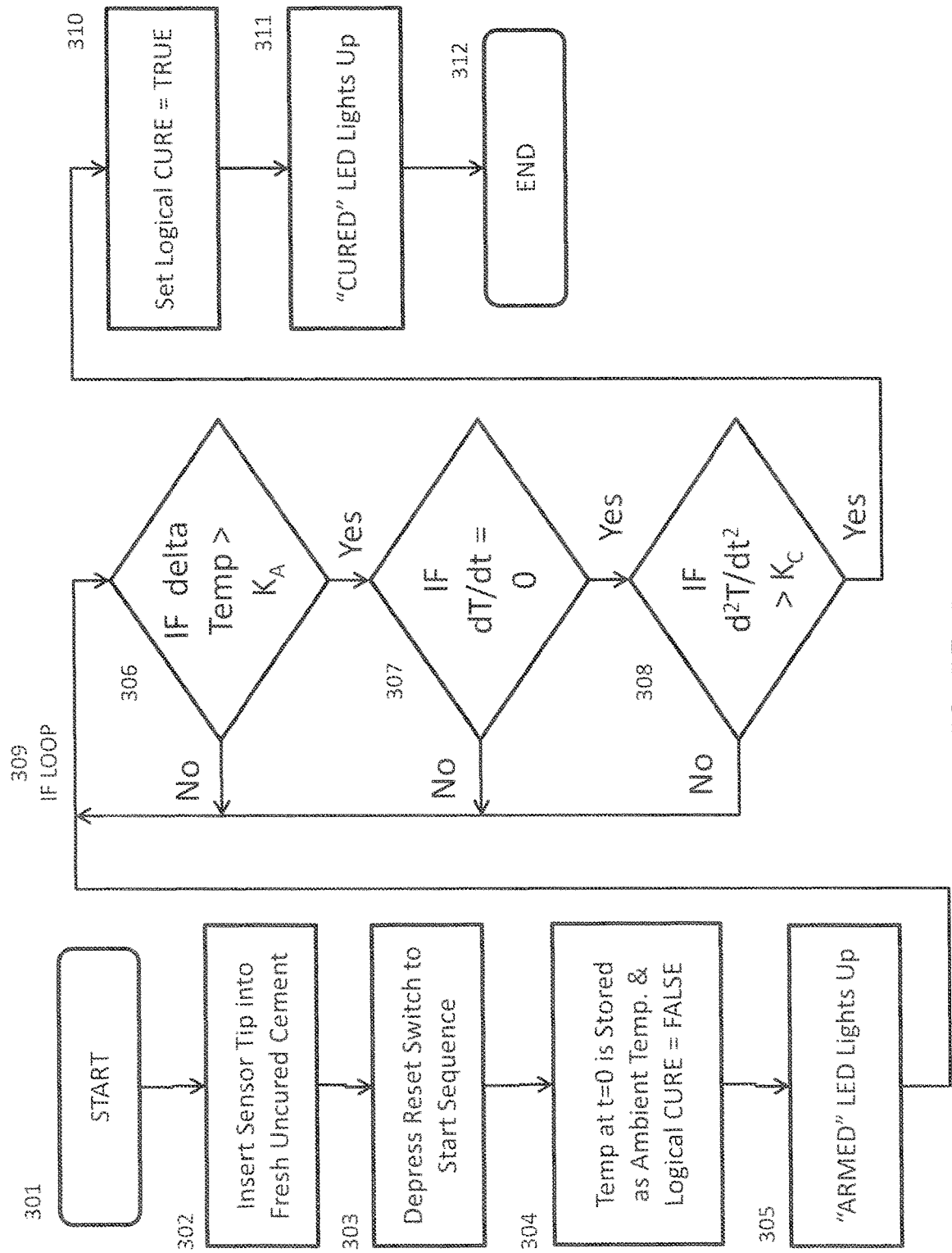
FIG. 17 shows a flowchart of the temperature sensor signal process steps.

FIG. 17 shows a flowchart for the determination of the cure point using a digital means provided by a programmable microcontroller unit (MCU). The flowchart starts at 301 and starts by having the sensor probe tip installed or mounted onto the bone and inserted into freshly mixed PMMA cement that is still soft and has not yet started to release any heat via its exothermic reaction at step 302. This usually takes about 5 minutes for the mixture to begin reacting and giving off heat which causes the cement mantle to rise in temperature. This period is typically used by the surgeon to apply the cement and to remove excess cement before the hardening process begins. The surgeon or operator then depresses the reset switch at step 303 and this clears any temporary data from the processing unit's memory, and in step 304, the initial temperature of the uncured PMMA is recorded and assigned as the ambient temperature at $t=t_0$, and the "ARMED" logical value is set as "TRUE" and the associated LED indicator is illuminated in step 305. The programmed microcode at this point is in a mode of continuously measuring the temperature of the cement mantle and comparing it against 3 tests using nested IF statements 306, 307, 308 in an IF loop 309. The three IF statements check to see if the measured temperature minus the initial ambient temperature (delta Temp) is greater than some nominal value $K_A$ (typically 3 C) in 306, and if the first derivative of the temperature with respect to time is zero which indicative of an inflection point in 307, and if the second derivative of the temperature with respect to time is positive relative a nominal value $K_C$ (usually a value circa 0.1 deg $C.^2/sec^2$) in 308. The derivatives are calculated using a discrete method with a sliding window of 3 cells. When all three IF conditions are met, then the logical "CURE" variable is set to "TRUE" in 310, and the "CURED" LED is illuminated in 311 and stays illuminated until the reset switch is depressed, and at this point, the program comes to an end in 312. This program, and its implementation in software for an MCU can also be implemented using analog processors with comparators and op-amps to achieve analog differentiation.

Figure 18:
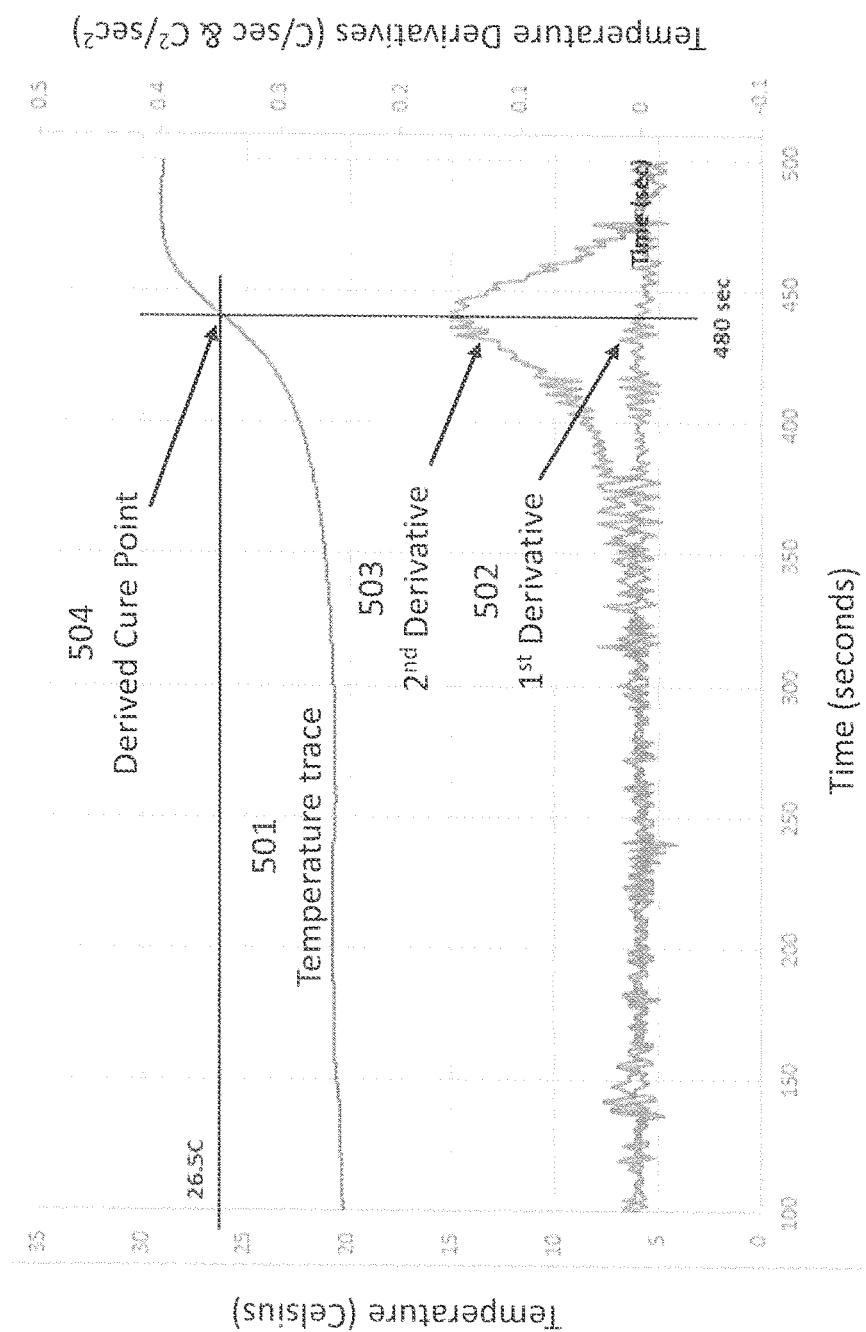
FIG. 18 shows the cement cure temperature and its first and second derivatives used to determine the exact time of the cure point.

FIG. 18 shows an example of measured data from a simulated bone and PMMA cement curing experiment showing the temperature trace 501, its first derivative 502, and its second derivative 503. The correlation of the three IF statements from FIG. 17 can be visually seen here whereby the peak of the first derivative 502 coincides with the zero crossing of the second derivative 503, and the delta temp from ambient of >3° C. at the derived cure point 504 occurring at 480 seconds and a temperature of 26.5° C. The cure point here is derived unambiguously, and with high confidence that it is not a false positive cure point.

The following example demonstrates the advantage of a method for determining the curing time for in vivo tray cement as compared to the prior art use of in vitro cement.

The temperature-versus-time plot of cement curing was determined using two implantable temperature sensors, one in a simulated implanted tibial tray and another in the remainder cement. Using the first derivative of the temperature-versus-time plot during cement polymerization provided the precise curing time for each condition. FIG. 19 illustrates the set-up for this experiment including a simulated in vivo sample of artificial bone 204 held in a water bath 502 and including a steel plate 500 to simulate a tibial tray.

In order to examine a statistically significant sample for the cure point of bone cement during cementing of a tibial tray across two conditions (simulated in-vivo and in-vitro), an independent samples t-test was conducted. To determine the sample size for the study, a power analysis was conducted using G*Power version 3.1.9.5 for Mac OS X, and to determine the amount of statistical power needed to find a medium effect (Cohen's d=0.50) for an independent samples t-test at the power of 0.80, found in Cohen (1998), it was recommended to use an overall sample size of 110. Accordingly, 110 participants (55 participants per group) was determined to provide sufficient power to detect an effect.

Accordingly, fifty-five tests under two conditions were run with dental methyl methacrylate cement mixed in the same ratio as the orthopedic cement. To simulate in vivo conditions of the implanted tibial tray in accordance with the first condition, a cancellous bone substitute (Sawbones, Vashon Island, WA, USA) was placed in a 90° F. circulating water bath with water 1 inch (2.54 cm) below the Sawbones surface. A simulated tibial tray of 4 mm stainless steel was implanted using a standard cement technique with a temperature sensor positioned in the cement mantel. A second sensor 600 was positioned in a portion of the remaining cement and left to cure at room temperature in accordance with the second condition. The temperature from both sensors was measured simultaneously beginning at 5 min after mixing and continued until 20 min after mixing. A laptop 103 was used as the CPU of the tester of the invention.

A 2-inch$^3$ 1522-09:7.5 cellular rigid foam sample ((Sawbones, Vashon Island, WA, USA) was used to simulate the cut cancellous bone surface of a tibia prepared for tibial implantation (FIG. 19). The foam bone was placed into a brass fixture that secured it at a constant height. A ⅜-inch (0.95-cm) hole was drilled into the center of the bone cube to a depth of 1 inch (2.54 cm). The testing tray substitute consisted of a 1×1.5-inch (2.54×3.81-cm) trays of 4-mm-thick 316 stainless steel. The bone-facing side of the tray was grit-blasted so that the roughness of the surface finish approximated a standard cemented implant. Attached to the bone-facing side of the tray was a 1-inch-long (2.54-cm), ⅜-inch-diameter (0.95-cm) tapered 316 stainless steel stem.

The water bath consisted of a 3-gal (11.36-L) fish aquarium with a submersible 500-W temperature controller (Hygger HG-921; Hygger, Shenzhen, China) rated to 0.1° F. accuracy. In the tank was a submersible 2.9-W filter pump rated at 220 L/h. The pump output was connected to a plastic tubing (inside diameter: ⅜ inch [0.95 cm]) exiting into a three-cup (708 cc) plastic storage container. An outflow opening was placed on the same side of the container as the inflow of the container to siphon water back into the aquarium. The inlet and outlet were positioned such that the top tube connection was 1 inch (2.54 cm) below the top of the container. During the operation, the plastic container acted as a water bath with constant temperature water flowing around the simulated cancellous bone 1 inch (2.54 cm) below the top surface.

The bone cement was modeled using dental denture acrylic, which has the same chemical formulation as orthopedic acrylic cement. The two-part mixture consisted of a liquid monomer (Jet Liquid; Lang Dental Manufacturing, Wheeling, IL, USA) and polymer powder (Bosworth Duz-All, 166264 W; Bosworth Company, Midland, TX, USA) and was used for each of the runs. Two extra runs were performed with DePuy SmartSet MV Bone Cement (Ref 3122-40, lots 841+9943, 8432635; DePuy Orthopedics, Warsaw, IN, USA) to test accuracy of the dental cement model. The dental cement was mixed in the same proportion by weight as the orthopedic cement (2 g polymer powder to 1 g monomer). The temperature of the test cement was monitored using a thin-film NTC thermistor (model TT6-10KCB-9-50; TEWA Temperature Thermistors, Ltd, Lublin, Poland) attached to an Arduino programable controller (board model UNO R3; Arduino, Cocos Island). The reproducibility of the system was determined to be −0.3° C. The controller had two channels (A and B) that could monitor two TEWA sensors simultaneously. The temperatures of both in vivo and in vitro cement were recorded at a rate of 1/s into an Excel spreadsheet.

The statistical testing consisted of fifty-five runs of dental cement. Previously we ran six runs of dental cement and two runs of SmartSet MV Cement. Each run was prepared and completed in the same manner. After preparation of the Sawbones block, the block was placed into the bath container with circulating water (FIG. 3) maintained at a constant temperature of 90° F. The water bath level was adjusted and maintained at 1 inch (2.54 cm) below the cement-implant interface. Prior to each run, the Sawbones block was placed in a water bath and rested for at least 5 min so that the temperature of the block equalized with the temperature of the water.

The acrylic cement was mixed by hand in a bowl for 2 min. It was then allowed to rest for 1 min. After resting, the cement was used to implant the steel base tray onto the top of the prepared Sawbones cube. The cement was applied to the top surface of the Sawbones block and the TEWA temperature sensor placed on top of the cement. A small square of thin porous polyethylene packing material was placed on top of the sensor to dampen the heat sink effect of the steel base tray. The cement was then placed on the bottom of the steel base tray, and the base tray was impacted onto the Sawbones block, ensuring that the TEWA temperature sensor remained in position. A TEWA sensor was then inserted into a 2-g globule of the remainder cement and placed on the workbench. The room temperature was maintained at 68° F.

The recording of the two sensors was performed simultaneously and ran from 5 min after the start of mixing of the cement to 20 min after starting mixing.

The dental cement temperature plots are illustrated in FIG. 20. The individual plots closely reproduced the plots used by ASTM for cure determination of cure with a period of minimal change proceeding to an exponential increasing temperature then decreasing temperature after reaching the maximum temperature ($T_{max}$). In this study, there was observable consistency in the shape of the temperature plots between runs for both in vivo and in vitro conditions. Although the plots were similar in shape, the $T_{max}$ reached by the two conditions in each run varied significantly. The dental cement $T_{max}$ for in the vivo condition varied from 2.73° C. to 22.63° C. with a mean of 9.74° C. and the $T_{max}$ for the in vitro cement condition varied from 34.33° C. to 43.26° C. with a mean of 34.33° C. In both conditions, as the temperature approached $T_{max}$ there was a flattening of the temperature plot into an arc type shape. As a result, the $T_{max}$ in the results could not be precisely determined and was considered an approximation. Uniformly the time to cure for the in vivo cement was significantly shorter than the time to cure for the in vitro cement.

The DePuy SmartSet MV cement plots are shown in FIG. 16. The SmartSet plot shapes were comparable to those of dental cement. The dental and SmartSet cement plots reached a similar $T_{max}$ for both cement conditions. Since there were only two runs of the SmartSet, further statistical analysis was not believed to be appropriate. However, the temperature plots produced by the SmartSet were similar in configuration to the dental cement. (FIG. 20). The study used dental cement as a substitute for bone cement and orthopedic SmartSet cement to verify this test condition. The cement cure plots were similar in configuration and reached similar $T_{max}$. We believe that this comparison between dental cement and SmartSet cement validates the use of the dental cement is an appropriate substitute.

The results showed that over fifty-five runs, the temperature profiles were consistent and that the in vivo cement cured well before the in vitro cement. The maximum value of the first derivative provided the precise curing time for each condition in each of the fifty-five runs. The curing time for the simulated in vivo tray cement was, on average, 5 minutes 26 seconds (95% confidence interval from 5 minutes 0 seconds to 5 minutes 52 seconds) faster than that of the external in vitro cement.

An independent samples t-test was conducted to evaluate whether there were significant differences in cement curing time between in-vivo and in-vitro cement. The results revealed that the curing time for in-vivo cement (M=7.66, SD=1.07) was significantly faster in comparison to the curing time for in-vitro cement (M=13.09, SD=1.18), 4108)=−25.20, p<0.001 (mean difference=−5.43). The effect size for this analysis (d=4.82) was found to exceed Cohen's (1988) convention for a large effect (d=0.80). Table 1 summarizes the results from the independent samples t-test.

TABLE 1

| Summary of Independent Samples t-test | | | | | | |
|---|---|---|---|---|---|---|
| | | | | Mean Difference | Std. Error of Difference | 95% CI |
| | t | df | p | | | Lower | Upper |
| Curing Time | −25.20 | 108 | .000 | −5.43 | 0.22 | −5.86 | −5.00 |

The results indicate that the in-vivo cement cured at a significantly faster rate in comparison to in-vitro cement. The magnitude of this effect was large, suggesting the difference is important. The significance level (alpha) is the probability of making a type 1 error (i.e., rejecting a true null). A p-value of <0.001 indicates the results are highly significant and there is less than one in a thousand chance of making a type 1 error (or being wrong).

Orthopedic surgeons performing total joint arthroplasty are aware of the thermal characteristics of acrylic bone cement. Previous studies on this phenomenon have primarily aimed to determine whether the heat generated by the curing cement causes biological damage. In vivo and in vitro studies have been performed to quantify the peak temperature of cement during curing. Techniques to lower the maximum temperature of curing cement have been proposed with the purpose of decreasing possible thermal tissue damage and these studies have not been used to determine the state of cure of the cement. Thus, we believe that the use of the temperature of the curing cement in a simulated in vivo condition to determine the curing time has not previously been studied and furthermore, comparing the cure point of cement in vivo and in vitro is novel.

In this experiment the $T_{max}$ varied considerably between each run and each condition. The $T_{max}$ of the in vivo conditions were consistently lower than the $T_{max}$ of the in vitro condition. This likely reflected the variable heat dissipation caused by both the steel tray and the simulated biologic environment.

The inconsistency of $T_{max}$ as well as the flattening of the temperature plot meant that it was not possible to use the ASTM definition of cement cure. However, the shapes of the plots were consistent with the ASTM plot which showed period of minimal change followed by an exponential increase of the temperature and then a reversal of the slope as the cement begins to cool. Using the fact that there was a dramatic change of temperature at time of cure, we concluded that using a derivative of the temperature plot would allow us to determine a precise time of cement cure.

The first derivative is a line tangent to a point on the plot and indicates the instantaneous rate of change of a plot line. In our experiment the higher the first derivative value, the faster the temperature is changing. A positive first derivative value means that the temperature is increasing, while a negative first derivative indicates that the cement is cooling. The inflection point where the first derivative changes from positive to negative indicates that the chemical reaction in the cement is slowing and the cement can be considered cured.

The first derivative (dY/dX) is mathematically derived from the following formula:

$$(((Temp_{now} - Temp_{Before}) + (Temp_{next} - Temp_{now}))/\Delta Time)/2.$$

The moving averaged first derivative values were calculated for each of the fifty-five dental cement runs. (FIG. 20). The peak value of the first derivative for all fifty-five runs in both conditions was determined. The time difference between the maximum value of the first derivative for the in vivo condition subtracted from the in vitro condition is the time difference between cure in each of the six runs. In our experiment, the difference in curing time between in vivo and in vitro conditions varied from a low of 3 min 30 s to a high of 8 minutes and 54 seconds. The mean time difference was 5 minutes 26 seconds (FIG. 22).

Figure 23:
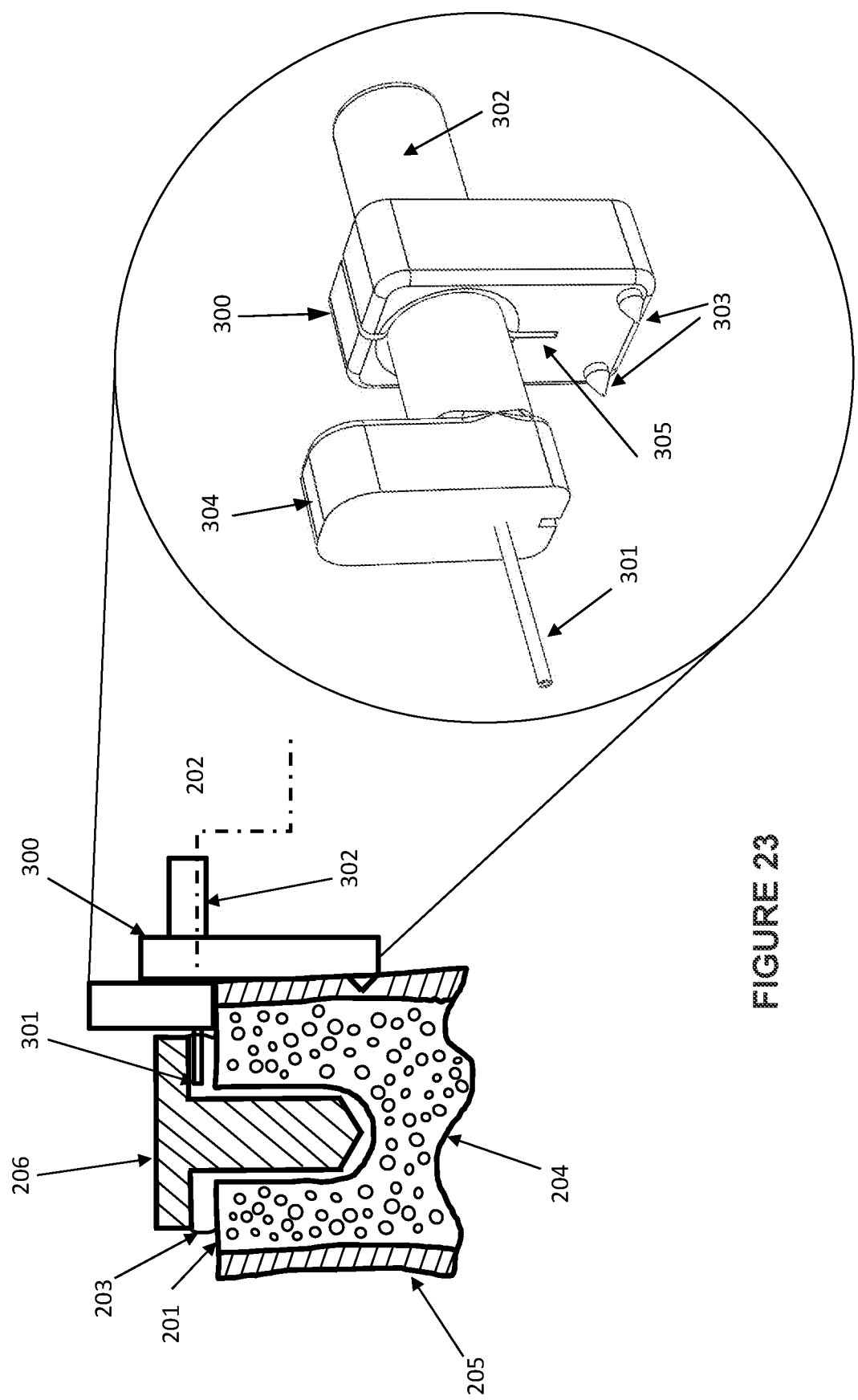
FIG. 23 shows a schematic diagram of an alternate embodiment of the present invention where the sensor probe is inside a conduit supported by a moveable sensor body held in place by a compact fixation jig utilizing sharp spikes.

FIG. 23 shows an alternate embodiment of a sensor holder fixture or jig that provides for an axially adjustable probe tip position through use of a compact sensor holder jig 300, provided with a split body to effect a clamping pressure on the moveable sensor body 302. The moveable body 302 position can be adjusted by manually clasping the hand grip 304 and sliding the body 302 relative to the holder jig 300. This allows for the precise positioning of hollow the probe tip 301 such that it pierces and enters into the cement mantle 203 that is in between the tibial plateau 201 and metal implant 206. The hollow conduit probe tip 301 can be made from a 21-gauge hypodermic needle (for example), and this provides a means of a protective sheath for the thermistor sensor mounted inside (not shown). In this way, the sensor conduit supports additional pressure to allow it to be axially inserted into the rather viscous cement mantle 203, such that the probe tip 301 does not mechanically buckle, fail, or deform beyond its elastic limit. The sensor jig 300 is fitted with one or more sharp metal spikes 303 that protrude and pierce the bone exterior 205 to provide a means of temporary fixation without the use of screws. The moveable sensor body 302 is hollow and houses the wire leads from the thermistor and their electrical joint with a more robust wire or sensor cable 202. The hollow cavity in 302 can be filled with a hardening electrically non-conductive potting compound to secure the wire joints and provide a hermetically sealed joint.

Based on our findings, it is true that the curing of the external cement is highly predictive of the curing of the in vivo cement. However, there is a significant time difference between the two curing points for in vivo and in vitro. In our study, the average curing time of the in vivo cement was 5 min 26 seconds faster than that of the in vitro cement. Our findings show that using the technique of waiting for the in vitro cement to cure can add unnecessary time to the surgical procedure. A technique to determine when the tibial tray cement is cured would be valuable in decreasing surgical time as well as decreasing the risk of aseptic loosening. We have demonstrated that the maximal temperatures reached by the cement during cure are inconsistent and that the $T_{max}$ is indistinct. Therefore, using the temperature values to determine cure during implantation may not be accurate. However, the use of the first derivative of the temperature plot provides a more precise point of full cure and could potentially be used intra-operatively to determine cement cure. This invention actually shows that the cure point in-vivo is not at a temperature X but a combination of the first and second derivative and some delta above ambient temperature. The temperature-versus-time plot of acrylic bone cement was utilized to determine the cure point of bone cement in two conditions during cementing of a tibial tray: simulated in vivo and in vitro. We found that in vitro cement took longer to cure than simulated in vivo cement, with an average duration of 5 min 26 s. Waiting for the external cement to cure before knee motion is a safe method to prevent lipid infiltration. Developing a method using temperature sensors to accurately determine tibial tray cement curing could safely shorten the surgical time of cemented total knee arthroplasty while decreasing the risk of lipid infiltration.

Although the present invention has been described based upon the above embodiments and the data produced by measurement of the performance of the resulting invention that has been reduced to practice, it is apparent to those skilled in the art that certain modifications, variations, and alternative constructions would be apparent, while remaining within the spirit and scope of the invention. In order to determine the metes and bounds of the invention, reference should be made to the following claims.

1. A system for securing an implant to a bone, comprising an implant, a grout or bone cement comprising a composition that cures in an exothermic reaction at a temperature x, the grout being capable of securing the implant to the bone in a cured state, and a sensor which detects the exothermic reaction to determine which the temperature reaches the temperature x, and comprises a sensor joined to a circuit and to an indicator that emits a signal in response to a current emitted to the circuit by the sensor.

2. A system for securing an implant to a bone as set forth in 1, wherein the signal is an audio signal, visual signal or haptic signal or signal to a robotic device.

3. A system for securing an implant to a bone as set forth in 1, further comprising a drill guide which provides access to the grout or bone cement in the bone.

4. A system for securing an implant to a bone as set forth in 1, wherein the drill guide is provided in a jig which is used to secure the implant within the bone.

5. A system for securing an implant to a bone as set forth in 1, wherein the grout or bone cement is an acrylate.

6. A system for securing an implant to a bone as set forth in 5, wherein the acrylate comprises methyl methacrylate.

7. A system for securing an implant to a bone as set forth in 1, wherein the bone is a human bone.

8. A system for securing an implant to a bone as set forth in 1, wherein the implant is an intermedullary implant.

9. A method for securing an implant to a bone, comprising: the steps of surgically exposing a bone and selecting an implant, applying an adhesive, grout or bone cement to the implant or to the bone, the adhesive, grout or bone cement comprising a composition that cures in an exothermic reaction at a temperature x, the adhesive being capable of securing the implant to the bone in a cured state, using a tester to determine the cure of the adhesive, the tester comprising a sensor in electrical contact with a circuit which is capable of conducting a current, and to an indicator that emits a signal in response to an increase in the current in the circuit.

10. A method for securing an implant to a bone as set forth in 9, wherein the signal is an audio signal.

11. A method for securing an implant to a bone as set forth in 9, wherein the signal is a visual signal.

12. A method for securing an implant to a bone as set forth in 9, wherein the signal is a haptic signal.

13. A method for securing an implant to a bone as set forth in 9, wherein the adhesive, grout or bone cement is an acrylate.

14. A method for securing an implant to a bone as set forth in 13, wherein the acrylate comprises methyl methacrylate.

15. A method for securing an implant to a bone as set forth in 9, wherein the bone is a human bone.

16. A method for securing an implant to a bone set forth in 9, wherein the implant is an intermedullary implant.

17. A method for securing an implant to a bone as set forth in 9, further comprising using a drill guide to provide access to a portion of the adhesive, grout or bone cement in situ.

18. A method for securing an implant to a bone as set forth in 17, wherein the drill guide is provided in a jig used to secure or position the implant in the bone.

19. A system as set forth in 1, that utilizes a digitally based signal processor utilizing an analog to digital converter (ADC) and a microcontroller unit (MCU) or other central processor unit (CPU) to determine the state of the cure.

20. A system as set forth in 19, that utilizes the relative temperature increase in the adhesive, grout, or cement, with respect to the ambient temperature to determine the state of cure.

21. A system as set forth in 19, that utilizes the first derivative of the temperature with respect to time to determine the state of cure.

22. A system as set forth in 19, that utilizes the second derivative of the temperature with respect to time to determine the state of cure.

21. A system as set forth in 19, that utilizes any combination of the first derivative of the temperature, the second derivative of the temperate with respect to time, and the relative temperature with respect to the ambient temperature to determine the state of cure.

22. A system as set forth in 19, that uses a compact electronic temperature sensor that is thin and flat in profile of approximate dimensions 0.5 mm thick×2 mm wide×25 mm to 50 mm long or is a cylindrical conduit and that is further comprised of a negative or positive resistive temperature coefficient sensor that is removable after cure.

23. A method of surgery including a step of securing an implant to a bone within a patient body by using a compound which undergoes an exothermic reaction during a process of curing, the method comprising: the steps of surgically exposing a bone, applying the compound to the implant or to the bone, the compound being capable of securing the implant to the bone in a cured state, using a tester in the applied compound within the patient body to determine the cure of the compound, the tester comprising a sensor which measures temperature over time.

24. The method of surgery as set forth in 23, wherein the tester is in electrical contact with a circuit which is capable of conducting a current.

25. The method of surgery as set forth in 24, wherein the tester is in electrical contact with an indicator that emits a signal in response to an increase in the current in the circuit.

26. The method of surgery as set forth in 23, wherein the tester further includes a microcontroller having the means to determine the rate chance of temperature over time, and including a step in which the derivative of the change in temperature over time is measured.

27. A method for securing an implant to a bone as set forth in 25, wherein the signal is an audio signal.

28. A method for securing an implant to a bone as set forth in 25, wherein the signal is a visual signal.

29. A method for securing an implant to a bone as set forth in 25, wherein the signal is a haptic signal.

30. A method for securing an implant to a bone as set forth in 23, wherein the compound is an acrylate.

31. A method for securing an implant to a bone as set forth in 23, wherein the acrylate comprises methyl methacrylate.

32. A method for securing an implant to a bone as set forth in 23, wherein the bone is a mammalian bone.

33. A method for securing an implant to a bone set forth in 23, wherein the implant is an intermedullary implant.

34. A method for securing an implant to a bone as set forth in 23, further comprising using a drill guide to provide access to a portion of the compound in situ.

35. A method for securing an implant to a bone as set forth in 34, wherein the drill guide is provided in a jig used to secure or position the implant in the bone.

36. A method as set forth in 23, wherein the tester utilizes a digitally based signal processor utilizing an analog to digital converter (ADC) and a microcontroller unit (MCU) or other central processor unit (CPU) to determine the state of the compound cure.

37. A method as set forth in 23, wherein the tester utilizes the relative temperature increase in the PMMA cement, with respect to the ambient temperature to determine the state of compound cure.

38. A method as set forth in 23, wherein the tester utilizes the first derivative of the temperature with respect to time to determine the state of compound cure.

39. A method as set forth in 23, wherein the tester utilizes the second derivative of the temperature with respect to time to determine the state of compound cure.

40. A method as set forth in 23, wherein the tester utilizes any combination of the first derivative of the temperature, the second derivative of the temperate with respect to time, and the relative temperature with respect to the ambient temperature to determine the state of compound cure.

41. A method as set forth in 23, wherein the tester comprises an electronic temperature sensor that is thin and flat in profile of approximate dimensions 0.5 mm thick×2 mm wide×25 mm to 50 mm long or is a cylindrical conduit and that is further comprised of a resistive temperature coefficient sensor that is removable after the procedure is over.

What is claimed is:

1. A system for securing an implant to a bone, comprising:
an implant,
a grout or bone cement in contact with the implant and comprising a composition that cures in an exothermic reaction at a temperature x, the grout being capable of securing the implant to the bone in a cured state, and
a tester in contact with the grout or bone cement and which detects the exothermic reaction to determine when the temperature reaches the temperature x, and comprises a sensor joined to a circuit which continuously monitors a change in temperature over time of the composition as compared to the ambient temperature and utilizes a first derivative of the relative temperature increase with respect to time with respect to an ambient temperature in the grout or cement to determine an inflection point in the rate of cure whereby the circuit activates a signal when it senses the inflection point of the temperature change.

2. The system for securing an implant to a bone as set forth in claim 1, wherein the signal is an audio signal, visual signal or haptic signal or signal to a robotic device.

3. The system for securing an implant to a bone as set forth in claim 1, further comprising a drill guide which provides access to the grout or bone cement in the bone.

4. The system for securing an implant to a bone as set forth in claim 1, wherein the drill guide is provided in a jig which is used to secure the implant within the bone.

5. The system for securing an implant to a bone as set forth in claim 1, wherein the grout or bone cement is an acrylate.

6. The system for securing an implant to a bone as set forth in claim 5, wherein the acrylate comprises methyl methacrylate.

7. The system for securing an implant to a bone as set forth in claim 1, wherein the bone is a human bone.

8. The system for securing an implant to a bone as set forth in claim 1, wherein the implant is an intermedullary implant.

9. The A system as set forth in claim 1, that utilizes a digitally based signal processor utilizing an analog to digital converter (ADC) and a microcontroller unit (MCU) or other central processor unit (CPU) to determine a state of the cement cure.

10. The system as set forth in claim 1, that utilizes a second derivative of the temperature with respect to time to determine the state of cure.

11. A system as set forth in claim 1, that uses a compact electronic temperature sensor comprised of a resistive temperature coefficient sensor that is removable after cure.

12. A system for securing an implant to a bone, comprising:
   an implant configured to be positioned with the bone,
   a grout or bone cement in contact with the implant and comprising a composition that cures in an exothermic reaction at a temperature x, the grout being capable of securing the implant to the bone in a cured state, and
   a tester in contact with the grout or bone cement and which detects the exothermic reaction to determine when the temperature reaches the temperature x, and comprises a sensor joined to a circuit which continuously monitors the change over time in temperature of the composition as compared to the ambient temperature to determine an inflection point at a rate change in the change in the relative temperature over time and utilizes a second derivative of the relative temperature increase with respect to time in the grout or cement with respect to the ambient temperature to determine a state of cure.

13. The system as set forth in claim 12 in which the tester comprises a thermistor.

14. The system as set forth in claim 12, that utilizes a digitally based signal processor utilizing an analog to digital converter (ADC) and a microcontroller unit (MCU) or other central processor unit (CPU) to determine the state of the cement cure.

15. The system as set forth in claim 14, wherein the thermistor measures a change in voltage and the MCU or CPU includes a circuit to determine the rate change in voltage as determined by the thermistor.

* * * * *